(12) United States Patent
Gray et al.

(10) Patent No.: US 7,344,559 B2
(45) Date of Patent: Mar. 18, 2008

(54) ELECTROMAGNETIC RADIATION TRANSPARENT DEVICE AND METHOD OF MAKING THEREOF

(75) Inventors: Robert W. Gray, Rochester, NY (US); Stuart G. MacDonald, Pultneyville, NY (US); Jeffrey L. Helfer, Webster, NY (US)

(73) Assignee: Biophan Technologies, Inc., Pittsford, NY (US)

( * ) Notice: Subject to any disclaimer, the term of this patent is extended or adjusted under 35 U.S.C. 154(b) by 475 days.

(21) Appl. No.: 10/923,292

(22) Filed: Aug. 20, 2004

(65) Prior Publication Data

US 2005/0049685 A1 Mar. 3, 2005

Related U.S. Application Data

(60) Provisional application No. 60/497,591, filed on Aug. 25, 2003.

(51) Int. Cl.
*A61F 2/06* (2006.01)

(52) U.S. Cl. ..................................... 623/1.15
(58) Field of Classification Search ...... 623/1.11–1.39; 600/3
See application file for complete search history.

(56) References Cited

U.S. PATENT DOCUMENTS

| | | | |
|---|---|---|---|
| 4,661,530 A | 4/1987 | Gogolewski et al. | |
| 4,830,003 A | 5/1989 | Wolff et al. | |
| 5,133,732 A | 7/1992 | Wiktor | |
| 5,170,802 A | 12/1992 | Mehra | |
| 5,320,100 A | 6/1994 | Herweck et al. | |
| 5,507,767 A | 4/1996 | Maeda et al. | |
| 5,630,829 A | 5/1997 | Lauterjung | |
| 5,702,419 A | 12/1997 | Berry et al. | |
| 5,725,572 A | 3/1998 | Lam et al. | |
| 5,727,552 A | 3/1998 | Ryan | |
| 5,824,045 A | 10/1998 | Alt | |
| 5,860,999 A | 1/1999 | Schnepp-Pesch et al. | |

(Continued)

FOREIGN PATENT DOCUMENTS

WO WO03015662 2/2003

OTHER PUBLICATIONS

Arno Buecker, et al., "Artifact-Free In-Stent Lumen Visualization by Standard Magnetic Resonance Angiography Using a New Metallic Magnetic Resonance Imaging Stent" Circulation, Apr. 16, 2002, pp. 1772-1775.

(Continued)

*Primary Examiner*—Suzette Gherbi
(74) *Attorney, Agent, or Firm*—Michael J. Nickerson; Basch & Nickerson LLP

(57) ABSTRACT

A medical device includes a pattern of electrically conductive material. The pattern of electrically conductive material has an anti-antenna geometrical shape such that the anti-antenna geometrical shape substantially prevents the medical device from creating an imaging artifact and/or substantially allows imaging of a volume within the medical device. The pattern may be formed by multiple "figure-8" shaped electrical conductors, multiple "figure-8" emulating electrical conductors, multiple sine-wave-like shaped electrical conductors, multiple zig-zag patterned electrical conductors, by multiple electrical conductors, each having sequential conductive loops, and/or a single conductor weaved into a loop mesh. The electrically conductive material may be titanium, tantalum, nitinol, stainless steel, and/or NbZr.

126 Claims, 14 Drawing Sheets

U.S. PATENT DOCUMENTS

| | | |
|---|---|---|
| 5,931,867 A | 8/1999 | Haindl |
| 6,032,063 A | 2/2000 | Hoar et al. |
| 6,033,436 A | 3/2000 | Steinke et at. |
| 6,074,362 A | 6/2000 | Jang et al. |
| 6,077,298 A * | 6/2000 | Tu et al. .................... 623/1.19 |
| 6,083,258 A | 7/2000 | Yadav |
| 6,117,167 A | 9/2000 | Goicoechea et al. |
| 6,123,722 A | 9/2000 | Fogarty et al. |
| 6,156,064 A | 12/2000 | Chouinard |
| 6,159,239 A | 12/2000 | Greenhalgh |
| 6,168,619 B1 | 1/2001 | Dinh et al. |
| 6,183,508 B1 | 2/2001 | Stinson et al. |
| 6,183,509 B1 | 2/2001 | Dibie |
| 6,221,099 B1 | 4/2001 | Andersen et al. |
| 6,221,100 B1 | 4/2001 | Strecker |
| 6,221,102 B1 | 4/2001 | Baker et al. |
| 6,224,625 B1 | 5/2001 | Jayaraman |
| 6,228,111 B1 | 5/2001 | Törmälä et al. |
| 6,231,516 B1 | 5/2001 | Keilman et al. |
| 6,238,491 B1 | 5/2001 | Davidson et al. |
| 6,241,691 B1 | 6/2001 | Ferrera et al. |
| 6,251,136 B1 | 6/2001 | Guruwaiya et al. |
| 6,272,370 B1 | 8/2001 | Gillies et al. |
| 6,280,385 B1 | 8/2001 | Melzer et al. |
| 6,325,822 B1 | 12/2001 | Chouinard et al. |
| 6,350,279 B1 | 2/2002 | McGuinness |
| 6,393,314 B1 | 5/2002 | Watkins et al. |
| 6,424,234 B1 | 7/2002 | Stevenson |
| 6,451,026 B1 | 9/2002 | Biagtan et al. |
| 6,471,645 B1 | 10/2002 | Warkentin et al. |
| 6,496,006 B1 | 12/2002 | Vrijheid |
| 6,501,978 B2 | 12/2002 | Wagshul et al. |
| 6,503,272 B2 | 1/2003 | Duerig et al. |
| 6,506,972 B1 | 1/2003 | Wang |
| 6,564,084 B2 | 5/2003 | Allred, III et al. |
| 6,606,513 B2 | 8/2003 | Lardo et al. |
| 6,628,980 B2 | 9/2003 | Atalar et al. |
| 6,673,999 B1 | 1/2004 | Wang et al. |
| 6,675,049 B2 | 1/2004 | Thompson et al. |
| 6,700,472 B2 | 3/2004 | Wang et al. |
| 6,701,176 B1 | 3/2004 | Halperin et al. |
| 6,712,844 B2 | 3/2004 | Pacetti |
| 6,713,671 B1 | 3/2004 | Wang et al. |
| 6,714,809 B2 | 3/2004 | Lee et al. |
| 6,765,144 B1 | 7/2004 | Wang et al. |
| 6,767,360 B1 | 7/2004 | Alt et al. |
| 6,815,609 B1 | 11/2004 | Wang et al. |
| 6,822,548 B2 | 11/2004 | Wang et al. |
| 6,824,512 B2 | 11/2004 | Warkentin et al. |
| 6,844,492 B1 | 1/2005 | Wang et at. |
| 6,846,985 B2 | 1/2005 | Wang et at. |
| 6,847,837 B1 | 1/2005 | Melzer et al. |
| 6,864,418 B2 | 3/2005 | Wang et al. |
| 6,876,886 B1 | 4/2005 | Wang |
| 6,898,454 B2 | 5/2005 | Atalar et al. |
| 6,906,256 B1 | 6/2005 | Wang |
| 7,048,716 B1 | 5/2006 | Kucharczyk et al. |
| 7,087,077 B1 * | 8/2006 | Van Dijk et al. .......... 623/1.15 |
| 2001/0044651 A1 | 11/2001 | Steinke et al. |
| 2002/0040185 A1 | 4/2002 | Atalar et al. |
| 2002/0107562 A1 | 8/2002 | Hart et al. |
| 2002/0111542 A1 | 8/2002 | Warkentin et al. |
| 2002/0138135 A1 | 9/2002 | Duerig et al. |
| 2002/0156515 A1 | 10/2002 | Jang et al. |
| 2002/0161421 A1 | 10/2002 | Lee et al. |
| 2002/0188345 A1 | 12/2002 | Pacetti |
| 2003/0018369 A1 | 1/2003 | Thompson et at. |
| 2003/0036776 A1 | 2/2003 | Foster et al. |
| 2003/0088178 A1 | 5/2003 | Owens et al. |
| 2003/0105509 A1 | 6/2003 | Jang et al. |
| 2003/0120148 A1 | 6/2003 | Pacetti |
| 2003/0135114 A1 | 7/2003 | Pacetti et al. |
| 2003/0135268 A1 | 7/2003 | Desai |
| 2003/0171670 A1 | 9/2003 | Gumb et al. |
| 2003/0199768 A1 | 10/2003 | Cespedes et al. |
| 2004/0077995 A1 | 4/2004 | Ferek-Petric et al. |
| 2004/0078067 A1 | 4/2004 | Thompson et al. |
| 2004/0093075 A1* | 5/2004 | Kuehne ...................... 623/1.15 |
| 2004/0138733 A1 | 7/2004 | Weber et al. |
| 2004/0143318 A1* | 7/2004 | Tseng et al. ............... 623/1.16 |
| 2004/0158310 A1 | 8/2004 | Weber et al. |
| 2004/0164836 A1 | 8/2004 | Wang et al. |
| 2004/0176822 A1 | 9/2004 | Thompson et at. |
| 2004/0181177 A1 | 9/2004 | Lee et al. |
| 2004/0210289 A1 | 10/2004 | Wang et al. |
| 2004/0225213 A1 | 11/2004 | Wang et al. |
| 2004/0249428 A1 | 12/2004 | Wang et al. |
| 2004/0249440 A1* | 12/2004 | Bucker et al. ............. 623/1.15 |
| 2004/0263172 A1 | 12/2004 | Gray et al. |
| 2004/0263173 A1 | 12/2004 | Gray |
| 2004/0263174 A1 | 12/2004 | Gray et al. |
| 2005/0004654 A1 | 1/2005 | Khosravi |
| 2005/0043761 A1 | 2/2005 | Connelly et al. |
| 2005/0080346 A1* | 4/2005 | Gianchandani et al. ..... 600/486 |
| 2005/0155779 A1 | 7/2005 | Wang et al. |
| 2005/0222642 A1 | 10/2005 | Przybyszewski et al. |
| 2005/0222647 A1 | 10/2005 | Wahlstrand et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0036311 A1* | 2/2006 | Nakayama et al. ........ 623/1.15 |
| 2006/0118319 A1 | 6/2006 | Wang et al. |
| 2006/0136039 A1 | 6/2006 | Martin |
| 2006/0282153 A1 | 12/2006 | Jang |
| 2007/0032862 A1* | 2/2007 | Weber et al. ............... 623/1.34 |
| 2007/0168016 A1* | 7/2007 | Gronemeyer et al. ...... 623/1.16 |
| 2007/0239256 A1* | 10/2007 | Weber et al. ............... 623/1.15 |

OTHER PUBLICATIONS

Lambertus W. Bartels et al., "MR Imaging of Vascular Stents: Effects of Susceptibility, Flow, and Radiofrequency Eddy Currents," published in Journal of Vascular and Interventional Radiology, vol. 12, No. 3, Mar. 2001, pp. 365-371.

Lambertus W. Bartels, et al., "Improved Luman Visualization in Metallic Vascular Implants by Reducing RF Artifacts," published in Magnetic Resonance in Medicine, 74:171-180 (2002).

Adam, M.D., et al., Interventional Magnetic Resonance Angiography, Seminars In Interventional Radiology, vol. 16, No. 1, 1991, at 31-37.

Amano, M.D., et al., Metallic Artifacts Of Coronary And Iliac Arteries Stents In MRI Angiography And Contrast-Enhanced CT, Clinical Imaging, vol. 23, No. 2, Mar./Apr. 1999, at 85-89.

Bakker, et al., MR-Guided Balloon Angioplasty: In Vitro Demonstration Of The Potential Of MRI For Guiding Monitoring, and Evaluating Endovascular Interventions, JMRI, vol. 8, Jan./Feb. 1998, at 245-250.

CDRH Magnetic Resonance Working Group, A Primer on Medical Device Interactions With Magnetic Resonance Imaging Systems, http://www.fda/gov/cdrh/ode/ primerf6.html, Mar. 5, 2000, at 1-18.

Colombo, M.D., et al., Biodegradable Stents "Fulfilling The Mission And Stepping Away" Circulation 2000, Jul. 25, 2000, 202:371-373 http://www.circulationaha.org.

De Cobelli, et al., MRI Assessment Of Coronary Stents Valutazione RMDelgi Stent Coronarici, RAYS, vol. 24, No. 1, 1999 at 140-148.

Duerinckx, M.D., et al., Assessment Of Coronary Artery Patency After Stent Placement Using Magnetic Resonance Angiography, JMRI, vol. 8, No. 4, Jul./Aug. 1998, at 896-902.

Friedrich, et al., Behavior Of Implantable Coronary Stents During Magnetic Resonance Imaging, International Journal of Cardiovascular Interventions, vol. 2, at 217-222.

Girard, et al., Wallstent Metallic Biliary Endoprosthesis: MR Imaging Characteristics, Radiology, vol. 184, No. 3, at 874-876.

Hilfiker, M.D, et al., Plain and Covered Stent-Grafts: In Vitro Evaluation Of Characteristics At Three Dimensional MR Angiography, Radiology, vol. 211, No. 3, Jun. 1999, at 693-697.

Hug, M.D. et al., Cornary Arterial Stents: Safety and Arifacts During MRI Imagining, Radiology 2000, vol. 216, Nov. 3, at 781-787.

Kee, M.D., et al, MR-Guided Transjugular Portosystemic Shunt Placement In A Swine Model, JVIR, vol. 10, No. 5, May 1999, at 529-535.

Laissy, et al., Magnetic Resonance Angiography of Intravascular Endoprotheses: Investigation Of Three Devices, Cardiovascular and Interventional Radiology, vol. 18, 1995, at 360-366.

Lardo, Ph.D., Real-Time Magnetic Resonance Imagining: Diagnostic and Interventional Applications, Pediatric Cardiology vol. 21, 2000, at 80-98.

Lenhart, M.D., et al., Stent Appearance at Contrast-Enhanced MR Angiography: In Vitro Examination with 14 Stents, Radiology Oct. 2000, vol. 271, No. 1, at 173-178.

Lufkin, et al., Interventional MRI: Update, European Radiology, vol. 7, (Suppl. 5), 1997 at 187-200.

Manke,C.; Stentagioplastie von Beckenarterienstenosen unter MRI-Kontrolle: Erste klinische Ergebnisse, Fotschr Rontgenstr, 2000:172, at 92-97.

Manke, MD, et al.; Magnetic Resonance Monitoring of Stent Deployment In Vitro Evaluation of Different Stent Designs and Stent Delivery Systems, Investigative Radiology, vol. 35, No. 6, Jun. 2000, at 343-351.

Matsumoto,et al.; Gadolinium Enhanced MR Imagining Of Vascular Stents, Journal of Computer Assisted Tomography, vol. 14, No. 3, May/Jun. 1990, at 357-361.

Matsumoto, et al., Tantalum Vascular Stents: In Vivo Evaluation With MR Imagining, Radiology, vol. 170, No. 3, Mar. 1989, at 753-755.

Nitatori, et al., MRI Artifacts of Metallic Stents Derived From Imaging Sequencing And The Ferromagnetic Nature Of Materials, Radiation Medicine, vol. 17, No. 4, 1999, at 329-334.

Omary, M.D. et al, MR-Guided Angioplasty Of Renal Artery Stenosis In A Pig Model: A Feasibility Study, J. JVIR 2000; vol. 11, at 373-381.

Schenck, The Role Of Magnetic Susceptibility In Magnetic Resonance Imaging: MRI Magnetic Compatibility Of The First and Second Kinds, Medical Physics, vol. 23, No. 6, Jun. 1996, at 815-850.

Shellock, Metallic Stents: Evaluation of MR Imaging Safety, AIR, vol. 173, Sep. 1999, at 543-547.

Strom, et al., safety Of Implantable Coronary Stents During 1 H-Magnetic Resonance Imaging at 1.0 and 1.5 T, Journal of Cardiovascular Magnetic Resonance vol. I, No. 3, 1999, at 239-245.

Stroman, et al., Will It Be Feasible To Insert Endoprostheses Under Interventional MRI?, J Endovasc-Surg, vol. 3, 1996, at 396-404.

Taal, et al., Potential Risks And Artifacts Of Magnetic Resonance Imaging Of Self-Expandable Esophageal Stents, Gastrointestinal Endoscopy, vol. 46, No. 5, 1997, at 424-429.

Tamai, M.D. et al., Initial and 6-Month Results of Biodegradable Poly-I-Lactic Acid Coronary Stents In Humans, Circulation, Jul. 25, 2000, at 399-404 http://www.circulationaha.org.

Tamai, M.D., et al., A Biodegradable Poly-I-Lactic Acid Coronary Stent In The Porcine Coronary Artery, Journal of Interventional Cardiology, vol. 12, No. 6, 1999 at 443-449.

Tsuji, MD, et al, Experimental and Clinical Studies of Biodegradable Polymeric Stents, Journal of Interventional Cardiology, vol. 13, Nov. 6, 2000, at 439-445.

* cited by examiner

ELECTROMAGNETIC RADIATION TRANSPARENT DEVICE AND METHOD OF MAKING THEREOF

PRIORITY INFORMATION

This application claims priority from U.S. Provisional Patent Application, Ser. No. 60/497,591, filed on Aug. 25, 2003. The entire content of U.S. Provisional Patent Application, Ser. No. 60/497,591 is hereby incorporated by reference.

FIELD OF THE PRESENT INVENTION

The present invention is directed to stent designs, deployment devices for stents, and the fabrications thereof. More particularly, the present invention is directed to stents which produce little or no magnetic resonance image artifacts and the fabrications thereof.

BACKGROUND OF THE PRESENT INVENTION

The use of stents as a medical corrective and preventive device is well known.

For example, U.S. Pat. No. 5,133,732 discloses that a stent can be implanted into a body vessel. The stent is a cylindrical body formed by a coiled generally continuous wire with a deformable zig-zag structure. The stent is further provided with means for preventing the stent body from stretching along its longitudinal axis. This stent is especially useful when implanting very long stents by means of balloon expansion. The entire content of U.S. Pat. No. 5,133,732 is hereby incorporated by reference.

In another example, U.S. Pat. No. 5,507,767 discloses that a self-expanding endovascular stent is formed of stainless steel wire which is bent into an elongated zigzag pattern. The zigzag pattern has a plurality of substantially straight wire sections of various lengths separating a plurality of bends. The zigzag pattern is helically wound about a central axis to define a tubular shape such that a majority of the bends is disposed in a helix. Adjacent bends in the helix are interconnected with a filament. The entire content of U.S. Pat. No. 5,507,767 is hereby incorporated by reference.

Magnetic resonance imaging ("MRI") has been developed as an imaging technique adapted to obtain both images of anatomical features of human patients as well as some aspects of the functional activities and characteristics of biological tissue. These images have medical diagnostic value in determining the state of the health of the tissue examined. Unlike the situation with fluoroscopic imaging, a patient undergoing magnetic resonance imaging procedure may remain in the active imaging system for a significant amount of time, e.g. a half-hour or more, without suffering any adverse effects.

In an MRI process, a patient is typically aligned to place the portion of the patient's anatomy to be examined in the imaging volume of the MRI apparatus. Such an MRI apparatus typically comprises a primary electromagnet for supplying a constant magnetic field ($B_0$) which, by convention, is along the z-axis and is substantially homogeneous over the imaging volume and secondary electromagnets that can provide linear magnetic field gradients along each of three principal Cartesian axes in space (generally x, y, and z, or $x_1$, $x_2$ and $x_3$, respectively). The MRI apparatus also comprises one or more RF (radio frequency) coils which provide excitation and detection of the MRI induced signals in the patient's body.

The gradient fields are switched ON and OFF at different rates depending on the MRI scan sequence used. In some cases, this may result in a changing magnetic field on the order of dB/dt=50 T/s. The frequency that a gradient field may be turned ON can be between 200 Hz to about 300 kHz.

Uniformity in the static magnetic $B_0$ field over the imaging volume is important for image clarity. When the field is not uniform, image distortions called "image artifacts" result. Additionally, if the gradient fields deviate significantly from their ideal linear character over the imaging volume, image artifacts develop.

Medical devices which are placed into a patient's body can cause the magnetic fields of the MRI system to deviate from their preferred characteristics for clear imaging. If a medical device comprises metallic components (such as iron), image artifacts result due to the metal's magnetic susceptibility properties distorting the MRI system applied magnetic fields. These are known as susceptibility artifacts. Additionally, if the medical device comprises conductive components, eddy currents develop in these conductive components when the MRI system's oscillating magnetic fields are applied. The eddy currents distort the net magnetic fields in the imaging volume, thereby providing another source for MR imaging artifacts.

After a stent is inserted into a patient, it is often desirable, over time, to determine if the stent is performing as expected. In the case, for example, of deploying a stent to correct a stenosis problem, it is desirable to determine if there is any indication of restenosis. This, as well as for other medical situations, requires obtaining images of the volume inside the stent. Due to the image artifact problems, described above, inherent in metallic, conductive stents, it is not possible to obtain clear MR images of the interior volume of the stents.

Attempts have been made to overcome these problems. The article, "Artifact-Free In-Stent Lumen Visualization by Standard Magnetic Resonance Angiography Using a New Metallic Magnetic Resonance Imaging Stent" by Arno Buecker, et al., *Circulation*, Apr. 16, 2002, pp. 1772-1775, discloses that a handmade stent can enhance the imaging ability of the stent's lumen. However, the handmade prototypes lacked a radial force comparable to standard stainless steel stents. Additionally, the article discloses the use of a contrasting agent to enhance visualization of the stent lumen.

The article "MR Imaging of Vascular Stents: Effects of Susceptibility, Flow, and Radiofrequency Eddy Currents" by Lambertus W. Bartels, et al., published in *Journal of Vascular and Interventional Radiology*, volume 12, Number 3, March 2001, pp. 365-371, describes the various image artifacts that prevent clear imaging of stent lumen.

The article "Improved Lumen Visualization in Metallic Vascular Implants by Reducing RF Artifacts" by Lambertus W. Bartels, et al., published in *Magnetic Resonance in Medicine*, 74:171-180 (2002), describes attempts at imaging metallic stents lumen by using contrast agents and by increasing the power deposited into the patient during the MRI procedure. The power deposited into the patient body, measured as the Specific Absorption Rate (SAR) can be harmful to the patient undergoing an MRI if set too high. In addition to the higher power deposited into the patient, the article discloses that adjustments in the image reconstruction process need to be implemented.

U.S. Patent Application Publication US 2002/0188345 A1, published Dec. 12, 2002, discloses an expandable metallic stent that has discontinuities of non-conducting material. These eliminate electrically conducting paths in the stent rings and cells. This makes the stent easier to image with magnetic resonance imaging (MRI). The entire content of U.S. Patent Application Publication US 2002/0188345 A1 is hereby incorporated by reference.

WIPO PCT publication WO 03/015662 A1 discloses that a metallic endoprosthesis causes no significant artifacts on images taken by magnetic resonance tomography (MRT), as a result of the combination of the production materials with a special design, which permits an evaluation of the externally adjacent region and the lumen of the endoprosthesis by means of MRT.

Although the above-described stents can be used to help a patient, these stents still cause magnetic resonance imaging artifacts. Moreover, the above-described stents prevent the imaging of the volume within the stent during magnetic resonance imaging.

Therefore, it is desirable to provide a stent which produces little to no magnetic resonance imaging artifacts. Moreover, it is desirable to provide a stent that allows the imaging of the volume within the stent. Furthermore, it is desirable to provide a stent which produces little to no magnetic resonance imaging artifacts and/or allows the imaging of the volume within the stent.

SUMMARY OF THE PRESENT INVENTION

One aspect of the present invention is a medical stent. The medical stent includes a pattern of electrically conductive material. The pattern of electrically conductive material has an anti-antenna geometrical shape such that the anti-antenna geometrical shape substantially prevents the medical stent from creating an imaging artifact.

Another aspect of the present invention is a medical stent. The medical stent includes a pattern of electrically conductive material. The pattern of electrically conductive material has an anti-antenna geometrical shape such that the anti-antenna geometrical shape substantially allows imaging of a volume within the stent.

Another aspect of the present invention is a medical stent. The medical stent includes a pattern of electrically conductive material. The pattern of electrically conductive material has an anti-antenna geometrical shape such that the anti-antenna geometrical shape substantially prevents the medical stent from creating an imaging artifact and substantially allows imaging of a volume within the stent.

Another aspect of the present invention is an electrically conductive structure. The electrically conductive structure includes a pattern of electrically conductive material. The pattern of electrically conductive material has an anti-antenna geometrical shape such that the anti-antenna geometrical shape substantially prevents creation of an imaging artifact by the electrically conductive structure.

Another aspect of the present invention is a medical device. The medical device includes a pattern of electrically conductive material. The pattern of electrically conductive material has an anti-antenna geometrical shape such that the anti-antenna geometrical shape substantially prevents creation of an imaging artifact by the medical device.

Another aspect of the present invention is an electrically conductive structure. The electrically conductive structure includes a pattern of electrically conductive material. The pattern of electrically conductive material has an anti-antenna geometrical shape such that the anti-antenna geometrical shape substantially allows imaging of a volume within the electrically conductive structure.

Another aspect of the present invention is an electrically conductive structure. The electrically conductive structure includes a pattern of electrically conductive material. The pattern of electrically conductive material has an anti-antenna geometrical shape such that the anti-antenna geometrical shape substantially prevents creation of an imaging artifact by the medical device and substantially allows imaging of a volume within the electrically conductive structure.

Another aspect of the present invention is a medical device. The medical device includes a pattern of electrically conductive material. The pattern of electrically conductive material has an anti-antenna geometrical shape such that the anti-antenna geometrical shape substantially allows imaging of a volume within the medical device.

Another aspect of the present invention is a medical device. The medical device includes a pattern of electrically conductive material. The pattern of electrically conductive material has an anti-antenna geometrical shape such that the anti-antenna geometrical shape substantially prevents creation of an imaging artifact by the medical device and substantially allows imaging of a volume within the medical device.

Another aspect of the present invention is a medical stent. The medical stent includes a pattern of electrically conductive material. The pattern of electrically conductive material substantially prevents the medical stent from creating an imaging artifact.

Another aspect of the present invention is a medical stent. The medical stent includes a pattern of electrically conductive material. The pattern of electrically conductive material substantially allows imaging of a volume within the stent.

Another aspect of the present invention is a medical stent. The medical stent includes a pattern of electrically conductive material. The pattern of electrically conductive material substantially prevents the medical stent from creating an imaging artifact and substantially allows imaging of a volume within the stent.

Another aspect of the present invention is an electrically conductive structure. The electrically conductive structure includes a pattern of electrically conductive material. The pattern of electrically conductive material substantially prevents creation of an imaging artifact by the electrically conductive structure.

Another aspect of the present invention is a medical device. The medical device includes a pattern of electrically conductive material. The pattern of electrically conductive material substantially prevents creation of an imaging artifact by the medical device.

Another aspect of the present invention is an electrically conductive structure. The electrically conductive structure includes a pattern of electrically conductive material. The pattern of electrically conductive material substantially allows imaging of a volume within the electrically conductive structure.

Another aspect of the present invention is an electrically conductive structure. The electrically conductive structure includes a pattern of electrically conductive material. The pattern of electrically conductive material substantially prevents creation of an imaging artifact by the medical device and substantially allows imaging of a volume within the electrically conductive structure.

Another aspect of the present invention is a medical device. The medical device includes a pattern of electrically conductive material. The pattern of electrically conductive material substantially allows imaging of a volume within the medical device.

Another aspect of the present invention is a medical device. The medical device includes a pattern of electrically conductive material. The pattern of electrically conductive material substantially prevents creation of an imaging artifact by the medical device and substantially allows imaging of a volume within the medical device.

Another aspect of the present invention is a medical stent. The medical stent includes a pattern of electrically conductive material. The pattern of electrically conductive material substantially prevents the medical stent from creating an imaging artifact. The electrically conductive material is shaped so as to be expandable, the expansion of the electrically conductive material causing an increase in a radius of the medical stent.

Another aspect of the present invention is a medical stent. The medical stent includes a pattern of electrically conductive material. The pattern of electrically conductive material substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a pattern of electrically conductive material. The pattern of electrically conductive material substantially prevents the medical stent from creating an imaging artifact and substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a pattern of electrically conductive material. The pattern of electrically conductive material substantially prevents the medical stent from creating an imaging artifact. The electrically conductive material is shaped so as to be expandable upon application of heat, the expansion of the electrically conductive material causing an increase in a radius of the medical stent.

Another aspect of the present invention is a medical stent. The medical stent includes a pattern of electrically conductive material. The pattern of electrically conductive material substantially allows imaging of a volume within the stent. The electrically conductive material is shaped so as to be expandable upon application of heat, the expansion of the electrically conductive material causing an increase in a radius of the medical stent.

Another aspect of the present invention is a medical stent. The medical stent includes a pattern of electrically conductive material. The pattern of electrically conductive material substantially prevents the medical stent from creating an imaging artifact and substantially allows imaging of a volume within the stent. The electrically conductive material is shaped so as to be expandable upon application of heat, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to substantially prevent the electrically conductive material from moving in such a way as to reduce the radius of the medical stent. The pattern of electrically conductive material substantially prevents the medical stent from creating an imaging artifact. The electrically conductive material is shaped so as to be expandable, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to substantially prevent the electrically conductive material from moving in such a way as to reduce the radius of the medical stent. The pattern of electrically conductive material substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to substantially prevent the electrically conductive material from moving in such a way as to reduce the radius of the medical stent. The pattern of electrically conductive material substantially prevents the medical stent from creating an imaging artifact and substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to allow the electrically conductive material to move in a single direction. The pattern of electrically conductive material substantially prevents the medical stent from creating an imaging artifact. The electrically conductive material is shaped so as to be expandable, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to allow the electrically conductive material to move in a single direction. The pattern of electrically conductive material substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a pattern of electrically conductive material and a track-and-lock mechanism having a shape substantially matching the shape of the electrically conductive material so as to allow the electrically conductive material to move in a single direction. The pattern of electrically conductive material substantially prevents the medical stent from creating an imaging artifact and substantially allows imaging of a volume within the stent. The electrically conductive material is shaped so as to be expandable, the expansion of the electrically conductive material causing an increase in a radius of the medical stent.

Another aspect of the present invention is a medical stent. The medical stent includes a plurality of links, each link being connected together so as to form a cylindrical shaped medical stent, each link being shaped so as to be expandable, the expansion of the links causing an increase in a radius of the medical stent.

Another aspect of the present invention is a medical stent. The medical stent includes a plurality of links, each link being connected together so as to form a cylindrical shaped medical stent, each link being shaped so as to be expandable upon application of heat, the expansion of the links causing an increase in a radius of the medical stent.

Another aspect of the present invention is a medical stent. The medical stent includes a plurality of links, each link being connected together so as to form a cylindrical shaped medical stent, each link being shaped so as to be expandable, the expansion of the links causing an increase in a radius of the medical stent; and a track-and-lock mechanism having a shape substantially matching the shape of the links so as to substantially prevent the links from moving in such a way as to reduce the radius of the medical stent.

Another aspect of the present invention is a medical stent. The medical stent includes a plurality of links, each link being connected together so as to form a cylindrical shaped medical stent, each link being shaped so as to be expandable upon application of heat, the expansion of the links causing an increase in a radius of the medical stent; and a track-and-lock mechanism having a shape substantially matching the shape of the links so as to allow the links to move in a single direction.

Another aspect of the present invention is a method of fabricating a medical stent. The method cuts a first cylinder of electrically conductive material so as to create a first pattern of conductive mesh strands having a plurality of nodes, cuts a second cylinder of electrically conductive material so as to create a first pattern of conductive mesh strands having a plurality of nodes, positions the first cylinder into a volume of the second cylinder and positioning the first cylinder with respect to the second cylinder such the nodes of the first cylinder are close to the nodes of the second cylinder without the nodes of the first cylinder touching the nodes of the second cylinder; and applies a non-conductive binding material to adjacent nodes of the two cylinders.

Another aspect of the present invention is a method of fabricating a medical stent. The method cuts a first cylinder of electrically conductive material so as to create a first pattern of conductive mesh strands having a plurality of nodes; cuts a second cylinder of electrically conductive material so as to create a first pattern of conductive mesh strands having a plurality of nodes; positions the first cylinder into a volume of the second cylinder and positioning the first cylinder with respect to the second cylinder such the nodes of the first cylinder are close to the nodes of the second cylinder without the nodes of the first cylinder touching the nodes of the second cylinder; positions a third cylinder of a non-conductive binding material between the first and second cylinders; and applies heat to the adjacent nodes of the first and second cylinders to cause the non-conductive binding material to bind the adjacent nodes together.

Another aspect of the present invention is a method of fabricating a medical stent. The method produces a web of conductive strands wherein at all the cross-over points, a non-conductive material is applied to hold the cross-over point strands in place and to electrically isolate the conductive strands from one another; cuts a portion of the web to produce a sheet of conductive strands, forms the sheet of conductive strands into a cylinder shape; and attaches ends of sheet together to hold the cylinder shape in place.

BRIEF DESCRIPTION OF THE DRAWINGS

The present invention may take form in various components and arrangements of components, and in various steps and arrangements of steps. The drawings are only for purposes of illustrating a preferred embodiment and are not to be construed as limiting the present invention, wherein.

DETAILED DESCRIPTION OF THE PRESENT INVENTION

Figure 1:
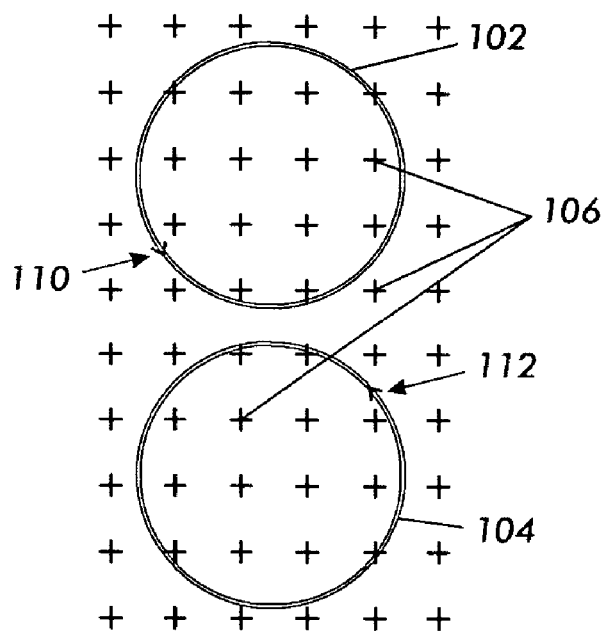
FIG. 1 is a schematic illustration of two conductive loops in a changing magnetic field.

The present invention will be described in connection with preferred embodiments; however, it will be understood that there is no intent to limit the present invention to the embodiments described herein. On the contrary, the intent is to cover all alternatives, modifications, and equivalents as may be included within the spirit and scope of the present invention, as defined by the appended claims.

For a general understanding of the present invention, reference is made to the drawings. In the drawings, like reference have been used throughout to designate identical or equivalent elements. It is also noted that the various drawings illustrating the present invention are not drawn to scale and that certain regions have been purposely drawn disproportionately so that the features and concepts of the present invention could be properly illustrated.

FIG. 1 is a schematic illustration of induced currents 110 and 112 in two conductive rings 102 and 104, respectively, when the conductive rings 102 & 104 are placed in an environment in which there is an oscillating magnetic field 106. At an instant in time, as illustrated in FIG. 1, both currents 110 & 112 travel in a clockwise direction. But as the magnetic field oscillates, the direction of these currents 110 & 112 will diminish to zero and then begin to circulate in a counter-clockwise direction (not shown.)

Figure 2:
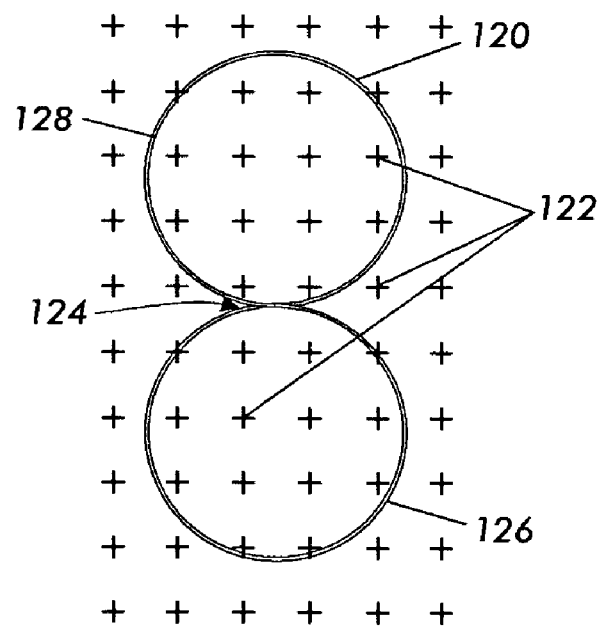
FIG. 2 is a schematic illustration of a conductor in a "figure-8" configuration in a changing magnetic field.
Figure 8:
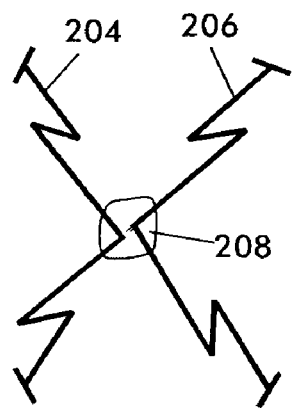
FIGS. 8 and 9 illustrate a stent mesh by a "Z"-like shape strand according to the concepts of the present invention.

FIG. 2 illustrates when the conductive rings 102 & 104 have been electrically joined together to form a single "figure-8" shaped or emulating conductor 120. The two lobes 126 & 128 of the "figure-8" shaped or emulating conductor 120 have equal planar areas. When placed in changing magnetic field 122 such that the flux of the magnetic field 122 passes through the lobes 126 & 128, no net current will be induced in the "figure-8" shaped or emulating conductor 120. The "figure-8" shaped or emulating conductor 120 is electrically insulated at the cross-over point 124.

Figure 3:
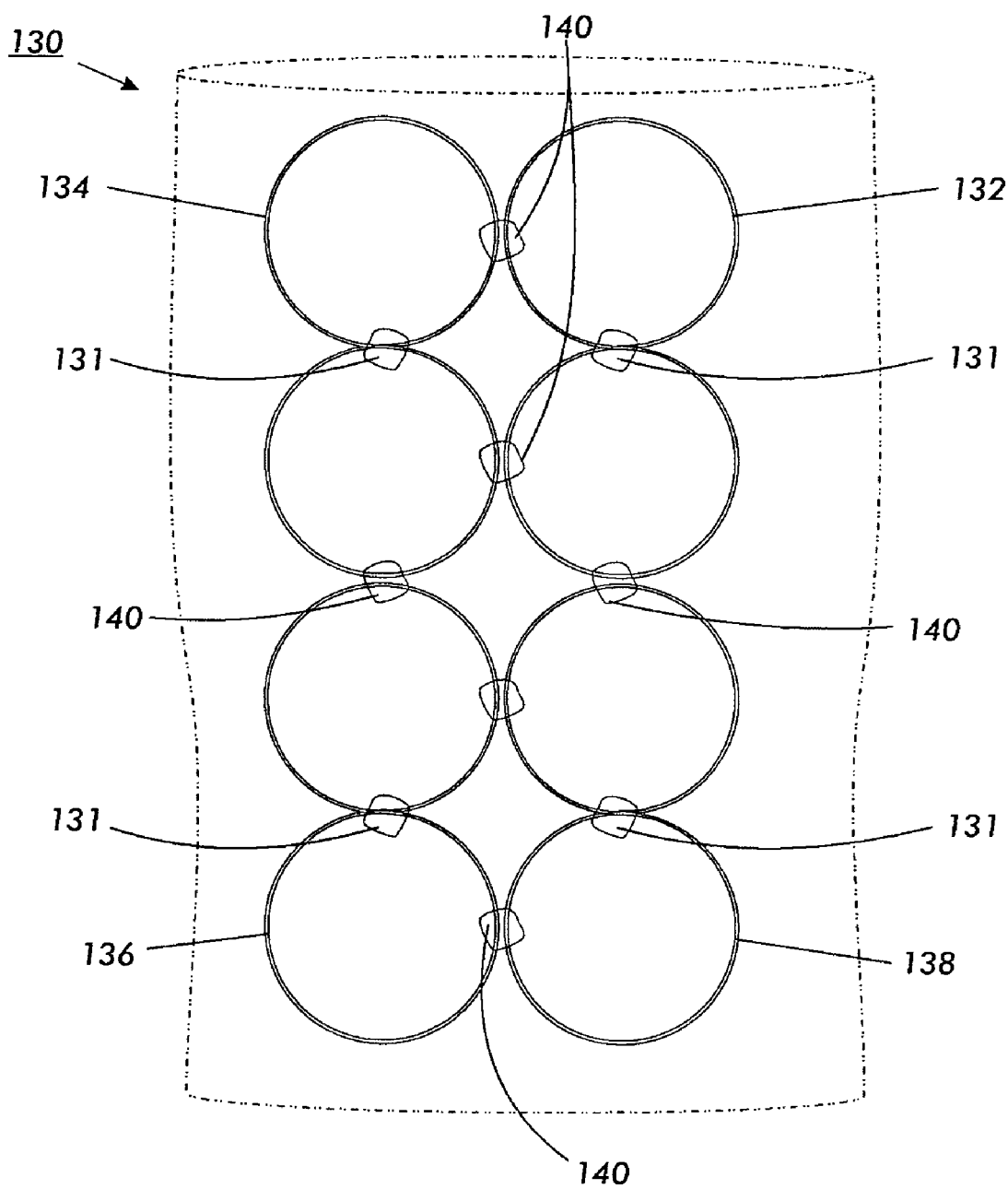
FIG. 3 is an illustration of one stent embodiment according to the concepts of the present invention.

FIG. 3 illustrates a portion of a medical stent 130, according to the concepts of the present invention. The illustrated medical stent 130 includes multiple "figure-8" shaped or emulating conductors 132, 134, 136 & 138. The "figure-8" shaped or emulating conductors 132, 134, 136 & 138 are electrically insulated at the cross-over points 131. The cross-over points 131 may also provide mechanical support for the "figure-8" shaped or emulating conductors 132, 134, 136 & 138

The "figure-8" shaped or emulating conductors 132, 134, 136 & 138 are fastened together by non-conductive connectors 140. These connectors 140 may be constructed of Teflon®, Tefzel®, a nonconductive polymer, silicon, or other nonconductive material. The "figure-8" shaped or emulating conductors 132, 134, 136 & 138 may be, for example, tantalum, nitinol, copper, or other conductive material or conductive composite material, which has a low magnetic susceptibility.

The "figure-8" shaped or emulating conductors realize immunity from the electromagnetic interference or insult. In other words, each "figure-8" shaped or emulating conductor has an anti-antenna geometrical shape such that the anti-antenna geometrical shape prevents the medical stent from creating an imaging artifact and/or allows the imaging of the volume within the stent.

Figure 4:
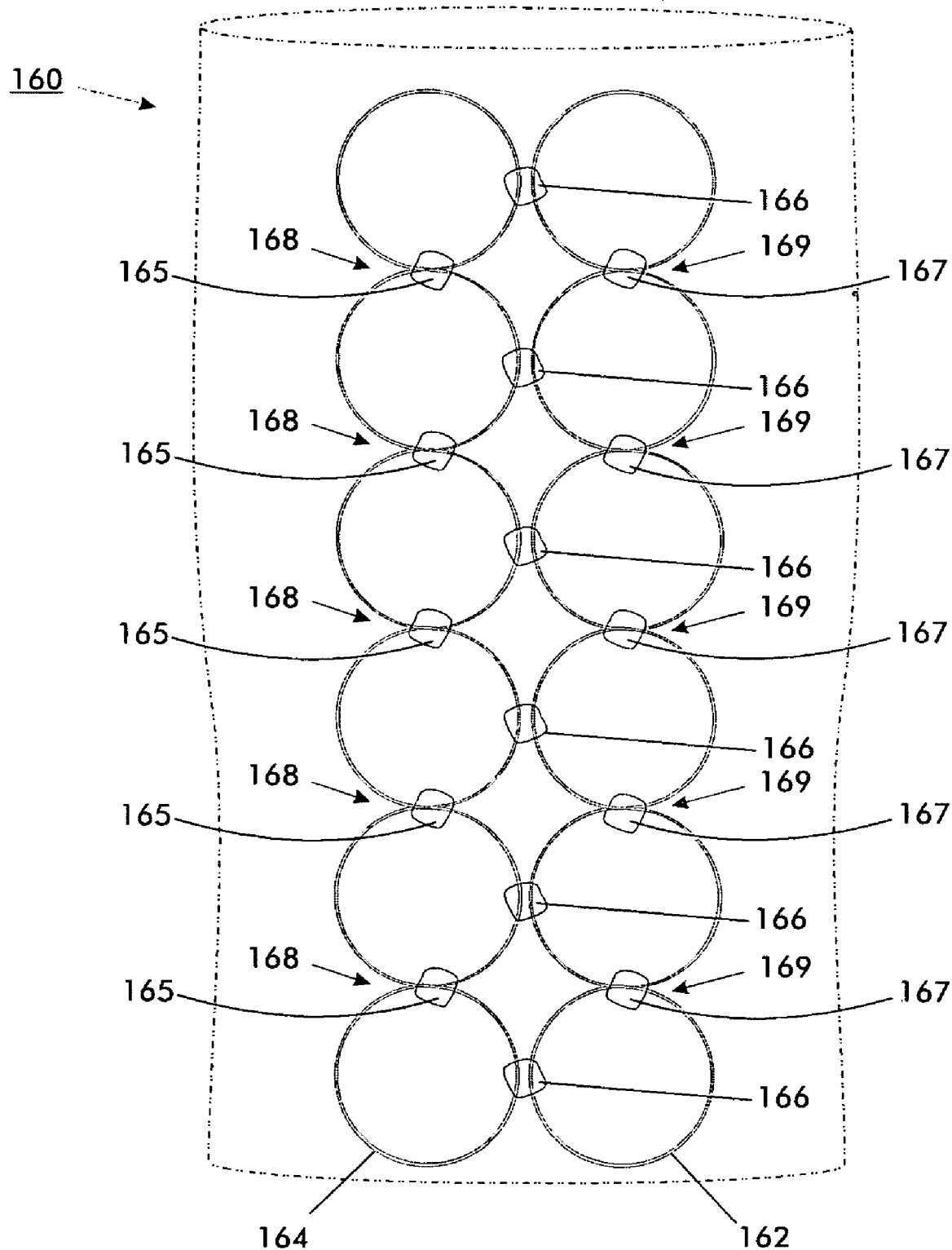
FIG. 4 is an illustration of another stent embodiment according to the concepts of the present invention.

FIG. 4 illustrates a portion of a medical stent 160, according to the concepts of the present invention. The illustrated medical stent 160 includes conductors 162 & 164 having sequential conductive loops to form the cylindrical surface of the medical stent 160. The sequential conductive loops form two or more sequential "figure-8" shaped or emulating conductive loop pairs wherein each sequentially looped conductor 162 & 164 contains an even number of loops.

At crossover point 168, the conductor 164 is electrically isolated by an insulation member 165 to prevent short circuiting the overall loop sequence. At crossover point 169, the conductor 162 is electrically isolated by an insulation member 167 to prevent short circuiting the overall loop sequence. The insulation members 165 and 167, at the crossover points 168 & 169, can also provide mechanical support for conductors 162 & 164 so that the shape is maintained.

The sequentially looped conductors 162 & 164 are fastened to each other using non-conductive material 166. Material 166 also provides means for securing the sequentially looped conductor 162 & 164 from slipping through the fasteners 166. Additional sequentially looped conductors (not shown) are added to complete the stent construction.

The sequentially looped conductors realize immunity from the electromagnetic interference or insult. In other words, each sequentially looped conductor has an anti-antenna geometrical shape such that the anti-antenna geometrical shape prevents the medical stent from creating an imaging artifact and/or allows the imaging of the volume within the stent.

Figure 5:
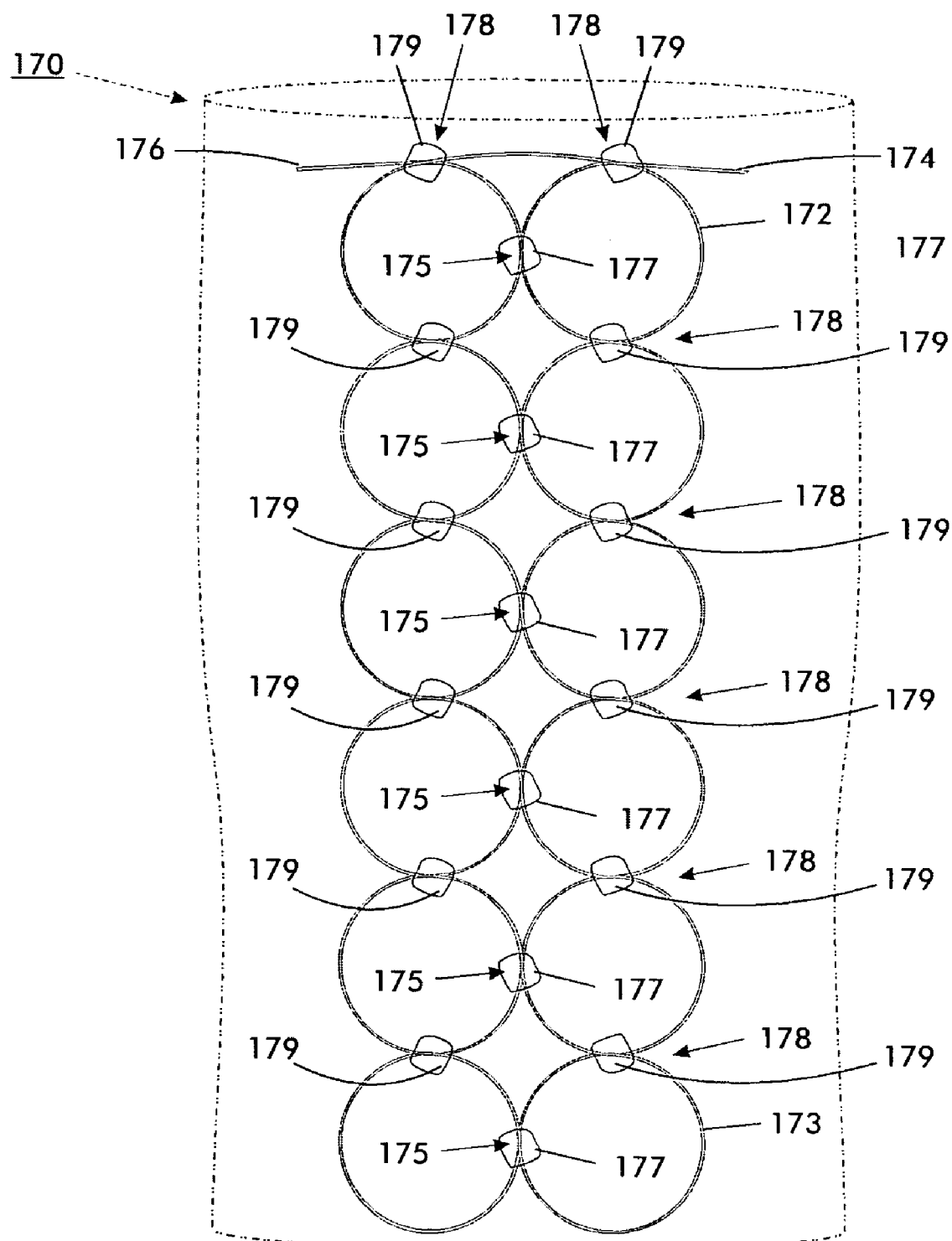
FIG. 5 is an illustration of another stent embodiment according to the concepts of the present invention.

FIG. 5 illustrates a portion of a medical stent 170, according to the concepts of the present invention. The illustrated medical stent 170 includes a single conductor 172 weaved into a loop mesh to define the stent cylinder. The weave, for example, beginning at 174, traces down the length of the to-be-constructed stent cylinder 170 and then back up the cylinder length to define an even number of loops. The pattern formed by the weave may be sinusoidal, "Z" shaped, zig-zag shaped, or sawtooth shaped or other such pattern that traverses back and forth with respect to a direction that is perpendicular to the progressive direction of travel of the trace. This pattern forms two or more runs of two or more sequential "figure-8" shaped or emulating conductive loop pairs wherein each run of two or more sequential "figure-8" shaped or emulating conductive loop pairs contains an even number of loops.

Continuing to follow the weave pattern, the conductor 172 continues to weave down and up the length of the cylinder to the point 176. To complete the stent, the weave continues in a like fashion around the circumference of the yet to-be-defined cylinder stent 170.

At each intra-run cross-over point 178, a nonconductive material 179 is used to electrically insulate the conductor 172 from itself. Additionally, the nonconductive material 179 secures the crossed-over conductor, along a run, from deforming or slipping or otherwise changing the intra-run cross-over points.

At each inter-run cross-over point 175, a nonconductive material 177 is used to electrically insulate the conductor 172 from itself. Additionally, the nonconductive material 177 secures the crossed-over conductor, between runs, from deforming or slipping or otherwise changing the inter-run cross-over points.

The weave pattern of the conductor realizes immunity from the electromagnetic interference or insult. In other words, the weave pattern has an anti-antenna geometrical shape such that the anti-antenna geometrical shape prevents the medical stent from creating an imaging artifact and/or allows the imaging of the volume within the stent.

Figure 6:
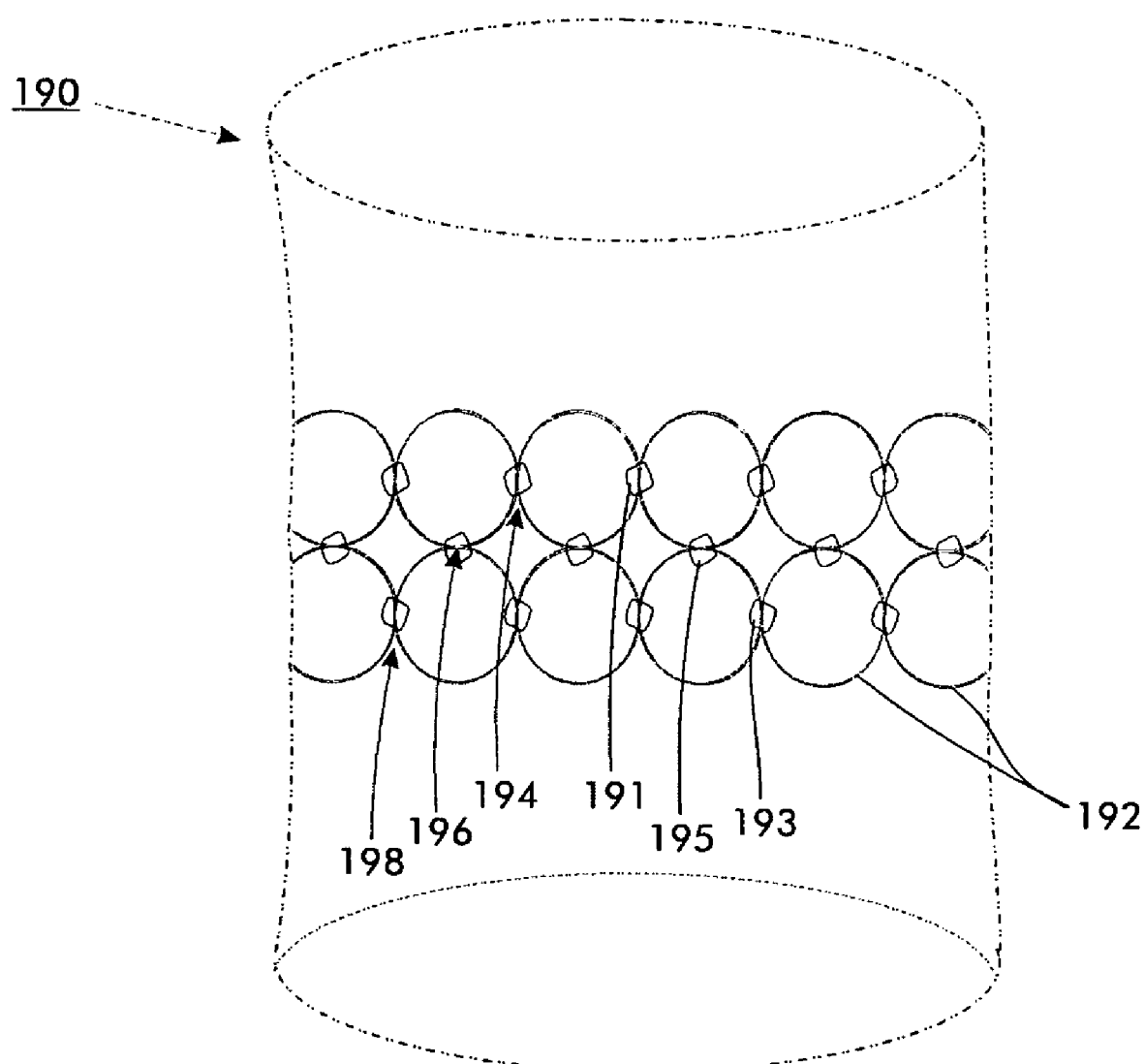
FIG. 6 is an illustration of another stent embodiment according to the concepts of the present invention.

FIG. 6 illustrates a portion of a cylinder shaped stent 190 being constructed from a single conductive material 192 in a weave pattern. In this case, the conductor completes a circumferential sine-wave-like pattern rather than the longitudinal sine-wave-like pattern shown in FIG. 5.

It is noted that the circumferential pattern formed by the weave may also be sawtooth or other such pattern that traverses back and forth with respect to a direction that is perpendicular to the progressive direction of travel of the trace.

At intra-run cross-over points 194 & 198, nonconductive materials 191 & 193 are used to electrically insulate the conductive material 192 from itself. Additionally, the nonconductive materials 191 & 193 secure the crossed-over conductive material 192, along a run, from deforming or slipping or otherwise changing the intra-run cross-over points.

At each inter-run cross-over point 196, a nonconductive material 195 is used to electrically insulate the conductive material 192 from itself. Additionally, the nonconductive material 195 secures the crossed-over conductive material 192, between runs, from deforming or slipping or otherwise changing the inter-run cross-over points.

The circumferential pattern realizes immunity from the electromagnetic interference or insult. In other words, the circumferential pattern has an anti-antenna geometrical shape such that the anti-antenna geometrical shape prevents the medical stent from creating an imaging artifact and/or allows the imaging of the volume within the stent.

Figure 7:
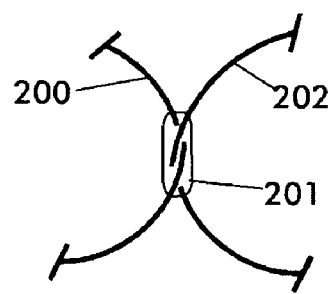
FIG. 7 illustrates a curved stent mesh embodiment according to the concepts of the present invention.
Figure 9:
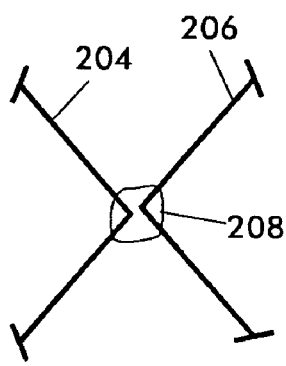

FIGS. 7-9 illustrate how the curved segments of the sine-wave like shape of the weaves mentioned in FIGS. 3, 4, 5, and 6 can be replaced by "Z" shaped, zig-zag shaped, or sawtooth shaped segments.

FIG. 7 shows a typical cross-over point of a stent weave. Conductors 200 and 202 (or a single conductor) of a stent weave are fastened together by a non-conductive material 201 which electrically insulates the conductors 200 and 202 (or a single conductor) from each other. It is noted that conductors 200 and 202 are continuous, not discontinuous, through non-conductive material 201.

FIG. 8 shows one possible alternative to the curved weave segments 200 and 202 of FIG. 7. In FIG. 8, the conductive segments have a "Z" shaped, zig-zag shaped, or sawtooth shaped. The conductive segments 204 and 206 do not cross over each other. The conductive segments 204 and 206 are fastened to each other by material 208 which electrically isolates conductive segments 204 and 206 from each other.

When the stent is to be positioned and expanded in the body, the "Z" shaped segments of conductive segments 204 and 206 straighten out to increase the overall diameter of the cylinder defined by the stent. This is shown in FIG. 9 wherein the conductive segments 204 and 206 have been straightened, thus increasing their span length and the overall diameter of the cylinder defined by the stent.

Figure 10:
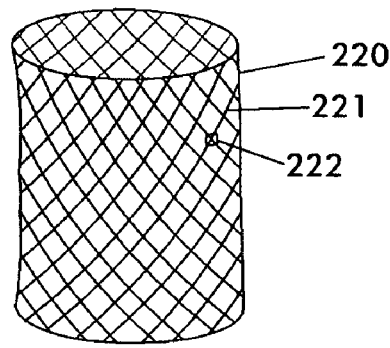
FIG. 10 illustrates a stent mesh embodiment according to the concepts of the present invention.

FIG. 10 shows a conductive cylinder medical stent 220 mesh comprising many conductive strands 221 and junctions 222. In this case, the conductors complete a sine-wave-like pattern. The pattern formed by the conductors may be circumferential or longitudinal. It is noted that the pattern formed by the conductors may also be "Z" shaped, zig-zag shaped, or sawtooth shaped or other such pattern that traverses back and forth with respect to a direction that is perpendicular to the progressive direction of travel of the trace.

The pattern formed by the conductors realizes immunity from the electromagnetic interference or insult. In other words, the pattern formed by the conductors has an anti-antenna geometrical shape such that the anti-antenna geometrical shape prevents the medical stent from creating an imaging artifact and/or allows the imaging of the volume within the stent.

Figure 11:
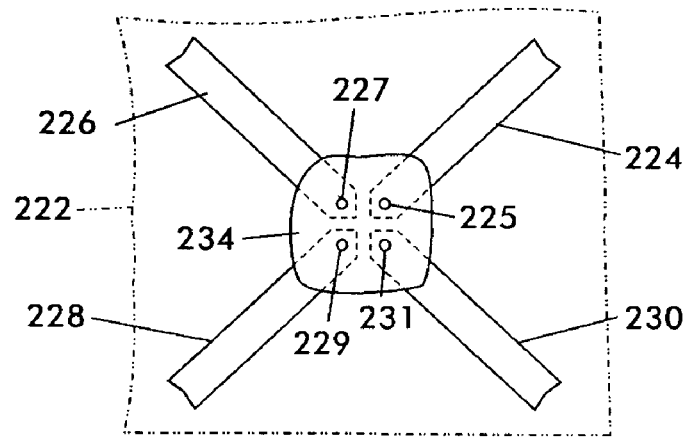
FIG. 11 illustrates a cross-over node in a stent mesh according to the concepts of the present invention.

FIG. 11 illustrates an expanded view of a junction 222, according to the concepts of the present invention. The junction 222 includes four conductive strands 224, 226, 228 & 230 fastened together and electrically isolated from one another by the non-conductive material 234. Small holes 225, 227, 229 & 231 are optionally fabricated into the ends of the conductive strands 224, 226, 228 & 230 so that the fastening material 234 may be shaped to include protrusions to securely fasten to the strands 224, 226, 228 & 230 with no possibility of any of the strands slipping out of the material 234.

It is noted that, although not shown, certain ends of the conductive strands 224, 226, 228 & 230 may be electrically connected to each other to form the proper loop circuitry needed to produce the opposing currents in the stent so that a net zero current is realized. For example, conductive strand 224 may be electrically connected to conductive strand 230, while conductive strand 226 may be electrically connected to conductive strand 228. On the other hand, for another example, conductive strand 224 may be electrically connected to conductive strand 226, while conductive strand 230 may be electrically connected to conductive strand 228.

The connection pattern of certain ends of the conductive strands realizes immunity from the electromagnetic interference or insult. In other words, the connection pattern of certain ends of the conductive strands has an anti-antenna geometrical shape such that the anti-antenna geometrical shape prevents the medical stent from creating an imaging artifact and/or allows the imaging of the volume within the stent.

Figure 12:
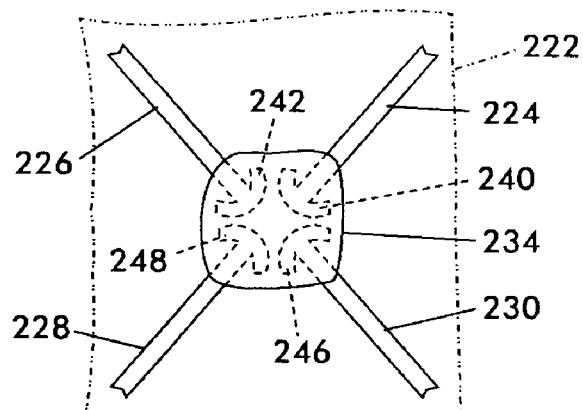
FIG. 12 illustrates another cross-over node in a stent mesh according to the concepts of the present invention.

Other shapes for the conductive strand ends to help secure the conductive strands 224, 226, 228 & 230 together, while keeping the conductive strands 224, 226, 228 & 230 electrically isolated, may be used. For example, FIG. 12 shows the conductive strands 224, 226, 228 & 230 with barbed ends 240, 242, 246 & 248, respectively, so that the fastening material 234 may be shaped around the barbed ends 240, 242, 246 & 248 to securely fasten to the strands 224, 226, 228 & 230 with no possibility of any of the strands slipping out of the material 234.

It is noted that, although not shown, certain of the barbed ends 240, 242, 246 & 248 of the conductive strands 224, 226, 228 & 230 may be electrically connected to each other to form the proper loop circuitry needed to produce the opposing currents in the stent so that a net zero current is realized. For example, conductive barbed end 240 may be electrically connected to conductive barbed end 242, while conductive barbed end 246 may be electrically connected to conductive barbed end 248. On the other hand, for another example, conductive barbed end 240 may be electrically connected to conductive barbed end 246, while conductive barbed end 248 may be electrically connected to conductive barbed end 242.

The connection pattern of certain barbed ends of the conductive strands realizes immunity from the electromagnetic interference or insult. In other words, the connection pattern of certain barbed ends of the conductive strands has an anti-antenna geometrical shape such that the anti-antenna geometrical shape prevents the medical stent from creating an imaging artifact and/or allows the imaging of the volume within the stent.

Figure 13:
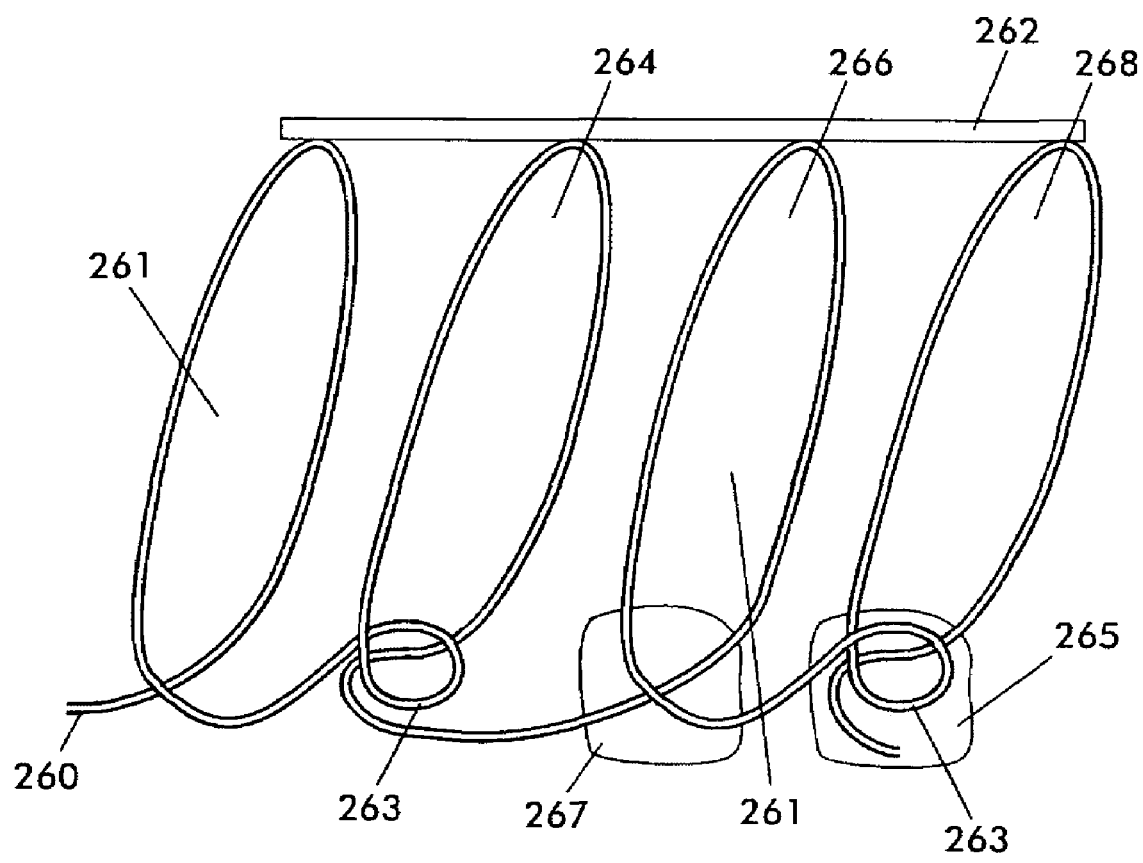
FIG. 13 illustrates another stent embodiment according to the concepts of the present invention.

FIG. 13 illustrates another type of conductive stent weave which can be employed as a stent or as a component of a stent. The conductor 260 is formed to produce a loop 261 that would have induced current flowing in a first direction, a loop 264 that would have induced current flowing in a second direction, a loop 266 that would have induced current flowing in the first direction, and a loop 268 that would have induced current flowing in the second direction, the first direction being opposite of the second direction. The direction changing pattern 263 enables the adjacent loops to have induced currents flowing in opposite directions.

An example of such a configuration is a loop-½ hitch-loop-½ hitch pattern wherein the ½ hitch would correspond to the direction changing pattern 263 of FIG. 13.

As illustrated in FIG. 13, stacking such loops 261, 264, 266, 268 . . . , with the interspersed direction changing pattern 263, forms a cylindrical coil. In this way, when following the conductor 260 from one end to the other, a trace would travel clockwise around the first loop 261, counter-clockwise around the next loop 264, clockwise around the next 266, counter-clockwise around the next 268, and so on.

At each cross-over point, nonconductive materials 267 & 265 are used to electrically insulate the conductive material 260 from itself. Additionally, the nonconductive materials 267 & 265 secure the crossed-over conductive material 260 from deforming or slipping or otherwise changing the cross-over points.

Optionally, non-conductive structural ribbing 262 may also be added to increase the structure strength and integrity of the overall stent.

The stacked loop pattern, with interspersed direction changing pattern, realizes immunity from the electromagnetic interference or insult. In other words, the stacked loop pattern, with interspersed direction changing pattern, has an anti-antenna geometrical shape such that the anti-antenna geometrical shape prevents the medical stent from creating an imaging artifact and/or allows the imaging of the volume within the stent.

Figure 14:
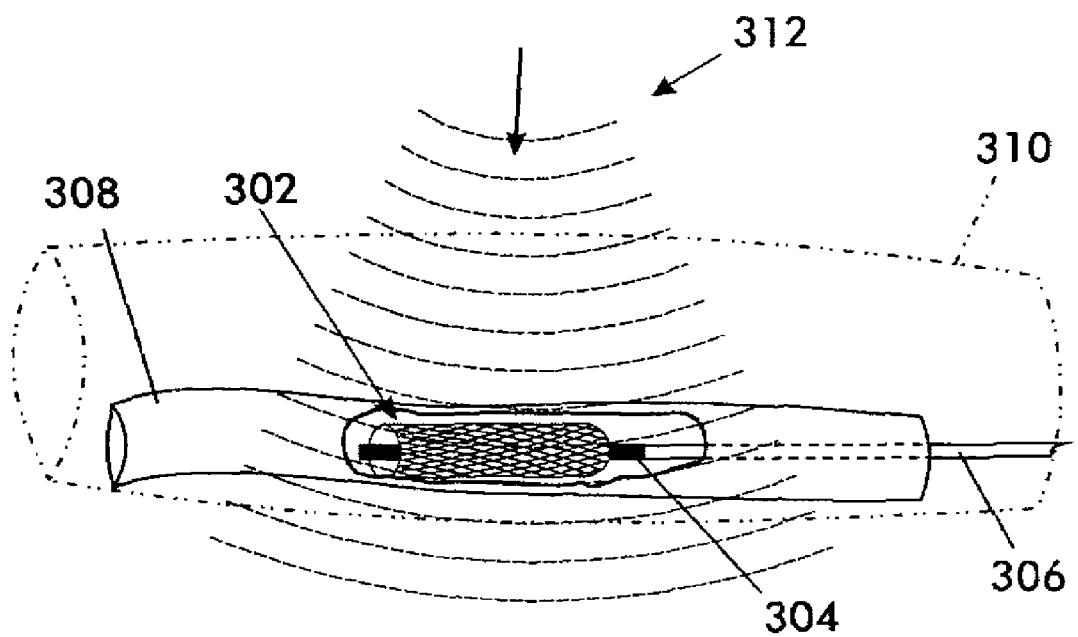
FIG. 14 illustrates a stent within a body which is heated by application of external RF energy.

FIG. 14 illustrates the deployment of an arterial stent 302. The arterial stent 302 is initially attached to a guidewire 306 at its distal end 304 and is positioned into place within a body 310 and within an artery 308. The arterial stent 302 is fabricated out of a memory material, for example, nitinol which, when heated, returns to a previous manufactured shape.

Initially the arterial stent 302 has a small cylindrical diameter. When RF energy 312 is transmitted through the body 310, the arterial stent 302 will heat up and expand to its final deployed diameter.

In one embodiment, the distal end 304 of the guidewire 306 is coated with a material which is particularly efficient at converting the RF energy 312 into heat energy to heat and activate the stent 302 expansion.

In another embodiment, the arterial stent 302, which may be a mesh or weave like stent as describe above, is coated with a material 322 (see FIG. 15) which is particularly efficient at converting the RF energy 312 (see FIG. 15) into heat energy. It is noted that the arterial stent 302 should be constructed to realize immunity from the electromagnetic interference or insult. In other words, the arterial stent 302 should be constructed to have an anti-antenna geometrical shape such that the anti-antenna geometrical shape prevents the medical stent from creating an imaging artifact and/or allows the imaging of the volume within the stent.

Figure 15:
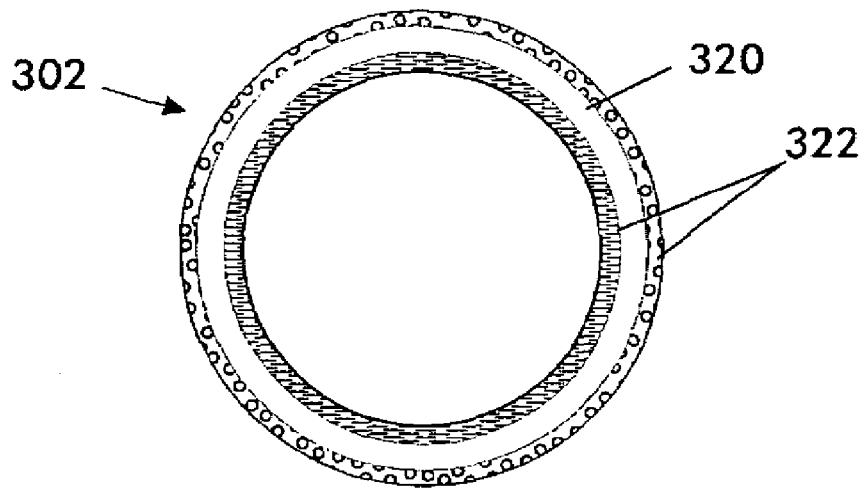
FIG. 15 is a cross sectional view of a coated stent according to the concepts of the present invention.

FIG. 15 shows a cross-section of the arterial stent 302 which is comprised of the stent mesh shape memory material 320 coated with heating material 322. Alternatively, only the outside of the stent mesh 320 is coated with the heating material 322. Alternatively, only the inside of the stent mesh 320 is coated with the heating material 322.

The RF energy 312 may be that which is transmitted by an MRI system (not shown) or may be that from some other RF transmitter (not shown). It is known that in some cases and under some conditions long conductors in an MRI environment can heat up. When this phenomenon is incorporated into the catheter or guide-wire which is part of the overall stent delivery system, this heat energy can be utilized to activate the shape memory material expansion, thus expanding the stent.

Figure 16:
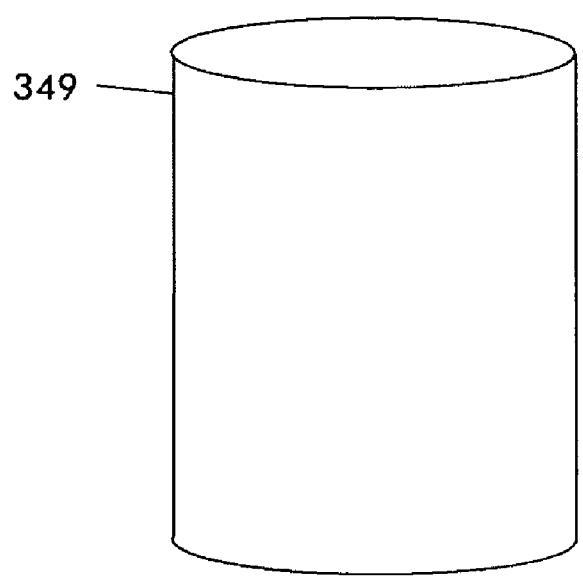
FIGS. 16 through 21 illustrate various steps in the creation of a medical stent according to the concepts of the present invention.
Figure 17:
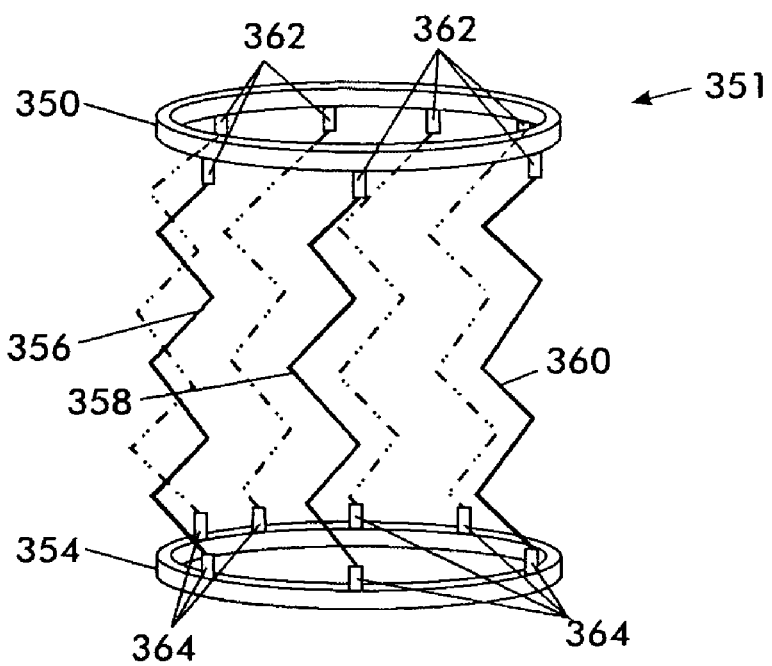

FIG. 16-21 illustrate one possible fabrication process for a medical stent. Referring to FIG. 16, the initial stock material 349; for example, tantalum; is in the shape of a hollow cylinder. The cylinder may be cut into a pattern as illustrated in FIG. 17, for example. The cutting of the cylinder stock material 349 may be accomplished by laser cutting or by other means.

FIG. 17 shows the resulting cut cylinder 351 which comprises end rings 350 and 354, and one half of the stent pattern mesh strands 356, 358 & 360. (Other mesh strands are shown as dashed lines for clarity.)

The mesh strands 356, 358 & 360 are connected to the end rings 350 & 354 by tabs 362 & 364.

Figure 18:
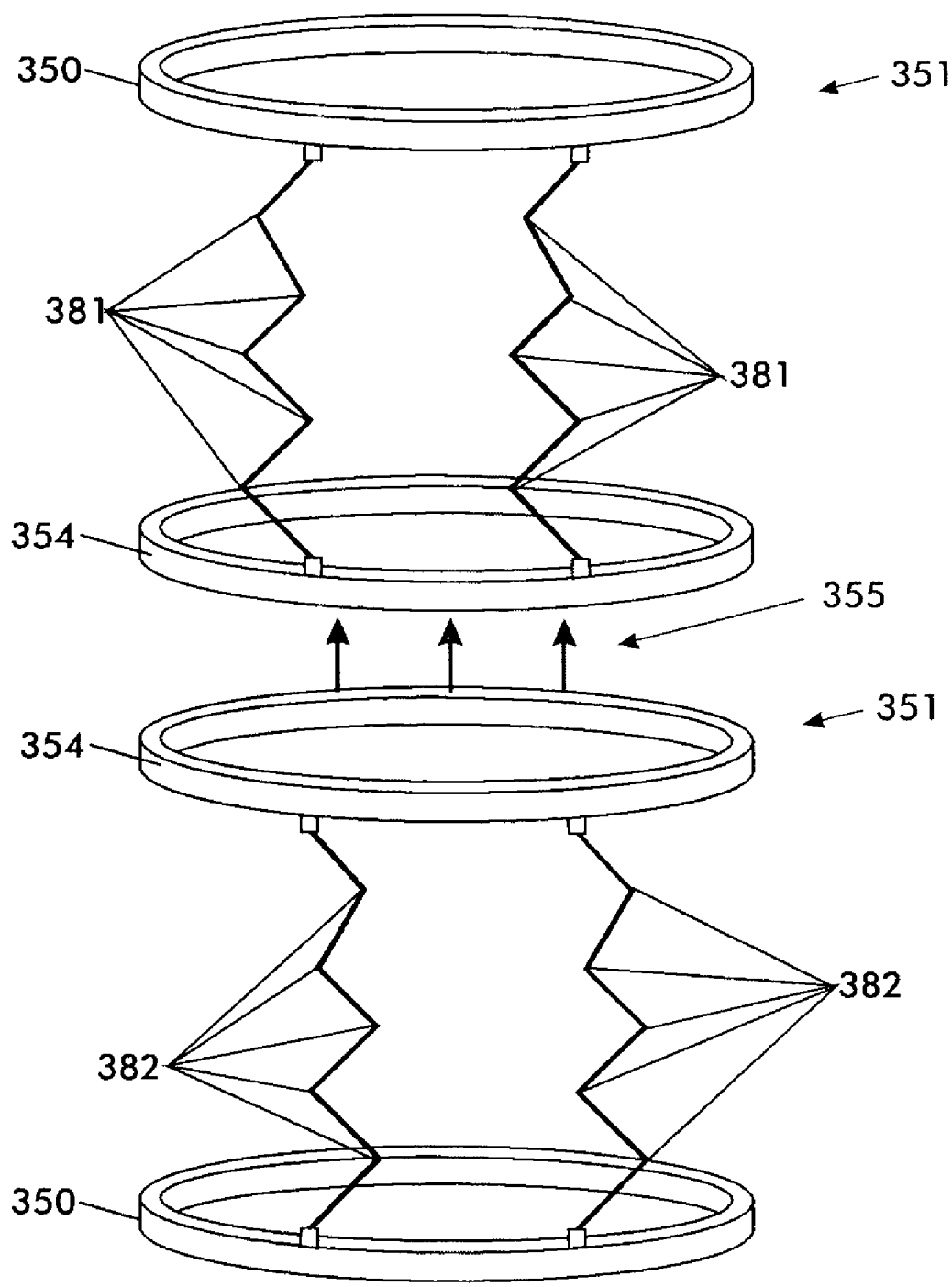

FIG. 18 shows two such cut cylinders 351 positioned such that one cylinder has been rotated by 180 degrees; so that the two end rings 354 are close to each other. As the arrows 355 in FIG. 18 illustrate, one cylinder is to be slid into the other. This may be accomplished in several different ways including: heating one of the cut cylinders so that it expands and/or fabricating one of the two cut cylinders out a cylinder stock material which is slightly smaller in diameter than the other.

Figure 19:
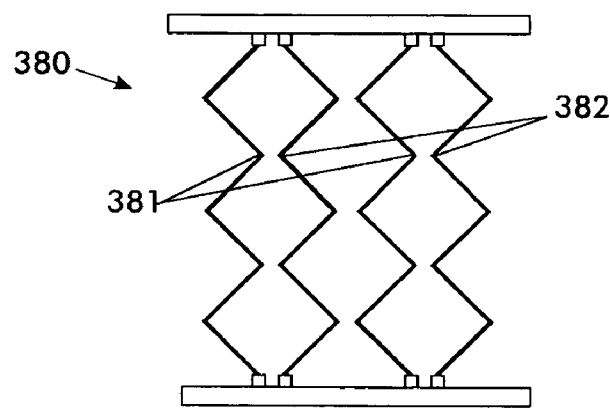

FIG. 19 illustrates the two cut cylinders in their final position. The orientation is such that the nodes in the cut pattern 381 & 382 are close together, but are not touching.

The two cut cylinders realize immunity from the electromagnetic interference or insult. In other words, the two cut cylinders have an anti-antenna geometrical shape such that the anti-antenna geometrical shape prevents the medical stent from creating an imaging artifact and/or allows the imaging of the volume within the stent.

Figure 20:
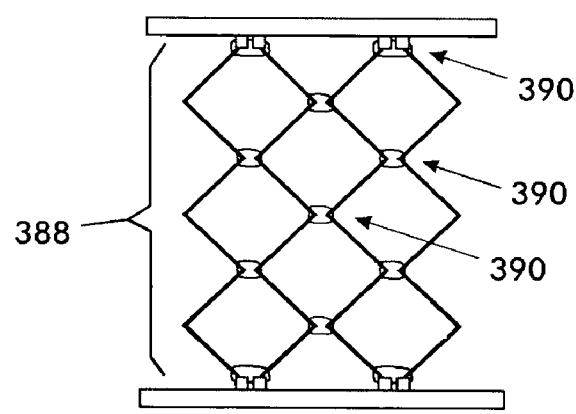
Figure 21:
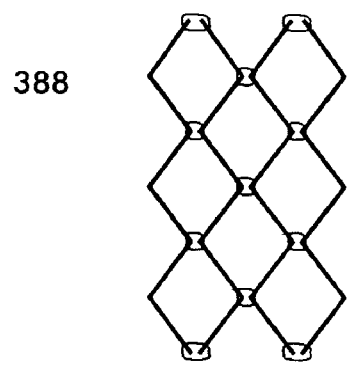

FIG. 20 illustrates the application of a non-conductive binding material 390, for example, silicon rubber or other thermoplastic or thermoset polymer, or glass, etc. at each of the nodes 381 & 382 which rigidly fasten the conductive mesh strands 356, 358 & 360 together. The resulting stent mesh 388 is then cut from the supporting nubs 362 & 364 of FIG. 17, giving the final stent portion 388 shown in FIG. 21.

The pattern that is cut out of the initial hollow cylinder stock of FIG. 16 may alternatively include "Z" shaped, zig-zag shaped, or sawtooth shaped segments as shown in FIG. 8 which facilitates the final stent's ability to expand radially.

In one embodiment (not shown, but referring to FIG. 21), the non-conductive binding material 390 of FIG. 20 is initially in the form of a hollow cylinder which is so dimensioned as to fit between the two cut cylinders 351 forming three concentric cylinders, the binding material 390 cylinder being the middle layer. The application of a laser or other means then melts the binding material 390 at the nodes as well as eliminates unwanted binding material.

Figure 22:
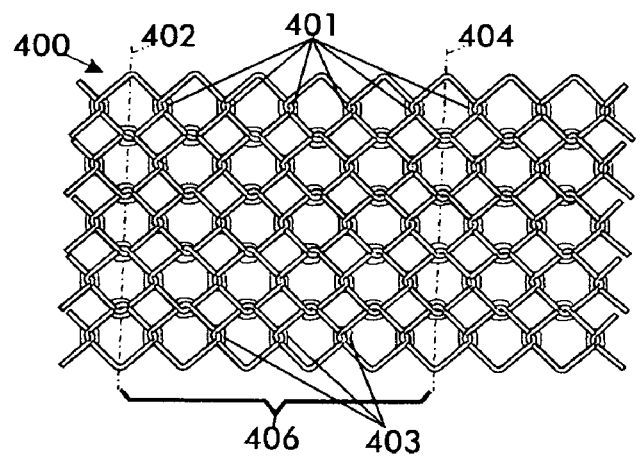
FIGS. 22 through 24 illustrate the use of a planar conductive weave sheet material from which a stent is formed according to the concepts of the present invention.

In one embodiment, the weaving of the conductive material (see, for example, FIG. 5) is used to produce a sheet stock planar material 400 illustrated in FIG. 22. As mentioned for other conductive weaves (see description of FIG. 5), at all the cross-over points, non-conductive materials 401 and 403 is applied to hold the cross-over point strands in place and to electrically isolate the conductive strands from one another. A portion 406 of the planar woven sheet or web is cut from the initial woven sheet 400. The dashed lines 402 and 404 indicate where a cut through the woven sheet or web 400 is made.

Figure 23:
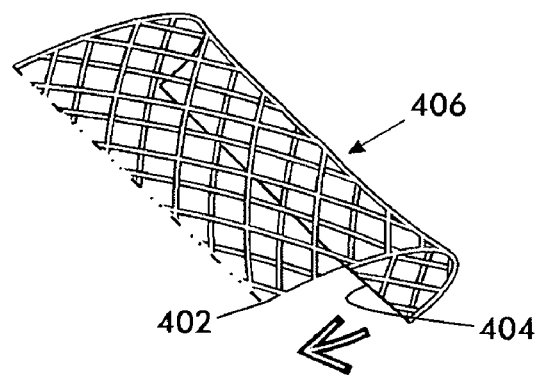
Figure 24:
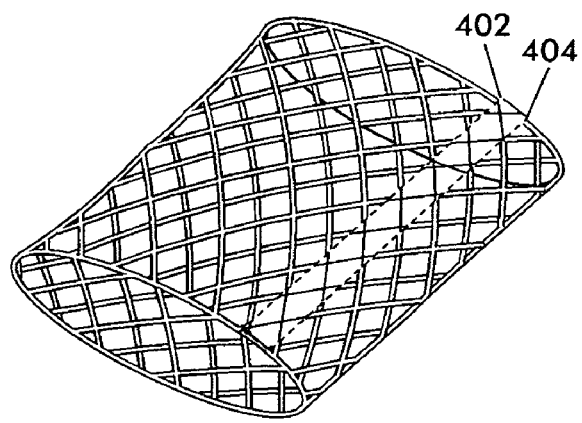

FIGS. 23 and 24 show the cut portion 406 being rolled into a cylinder shape. The cut strand, which come together as the cut edges 402 and 404, are brought together and then attached to one another to hold the stent together. The attachment may be affected by either a conductive material (solder, welding, etc.) or by a non-conductive means (glass, polymer, etc.)

In one embodiment (not shown) conductive metallic stents are coated with a nano-magnetic thin film coating which reduces the amount of eddy currents generated by the oscillating magnetic fields of an MRI system. In one such embodiment, multiple lays of various compositions and/or thicknesses are applied to the stents. In another embodiment, only portions of the stent are coated with the nano-magnetic thin films, thus changing the MRI system induced eddy current flow pattern.

In one embodiment, non-magnetic stents are coating with a nano-magnetic thin film coating which alters the magnetic fields of the MRI system enough for the stent to be visible in an MR image without distorting the image of the tissue a short distance from the stent.

In another embodiment (not shown) conductive metallic stent is coated with a carbon composite material, in part, in patterns, or in whole.

In another embodiment (not shown) non-conductive stents are coated with a carbon composite material, in part, in patterns, or in whole.

Figure 25:
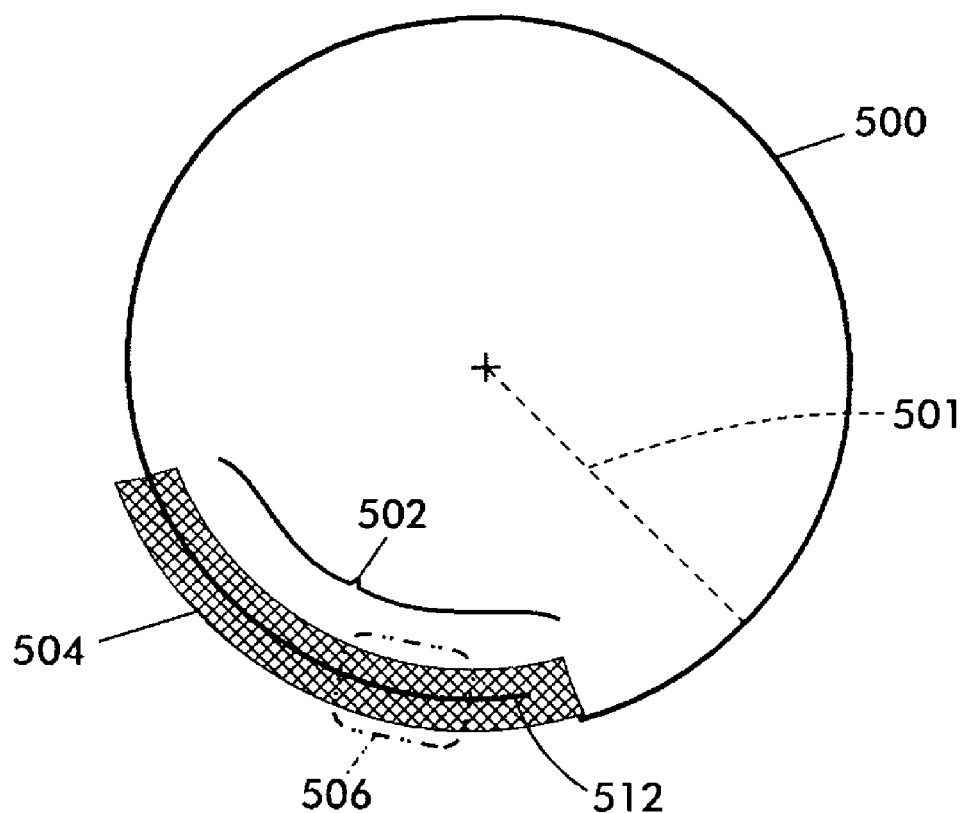
FIGS. 25 and 26 illustrate a locking mechanism for an expandable stent according to the concepts of the present invention.
Figure 26:
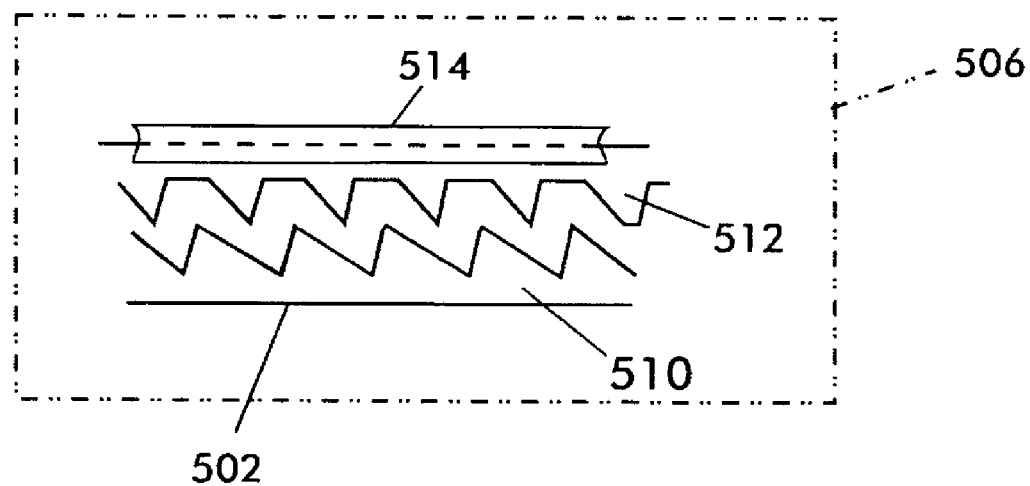

FIGS. 25 and 26 illustrate a stent 500 which is, initially, at its smallest radius "r" 501. The stent 500 is in the shape of a cylinder.

FIG. 25 illustrates a cross section of the stent 500. A stent strand 512 is wrapped within the stent 500 to reduce the cylindrical radius 501 before deployment with a body. The stent 500 has a track-and-lock mechanism 502 through which stent strand 512 passes and is confined to.

FIG. 26 gives one example of a track-and-lock mechanism 502. A portion 506 of the track-and-lock mechanism 502 is shown as a cut-away view in FIG. 26. The stent strand 512 has teeth which match that of the teeth 510 within the track-and-lock mechanism 502. The stent strand 512 is confined to move in the guide slot 514 and can only move in such a way so as to increase the overall radius 501 of the cylinder stent 500.

The shape of the teeth of the stent strand 512 and the shape of the teeth of the track-and-lock mechanism 502 prevent the stent strand 512 from moving in such a way as to reduce the cylinder radius 501. Thus, when deployed with; e.g. a balloon catheter system (not shown); the stent may be expanded to its full and final radius and locked into that radius.

In summary, the various stent embodiments, described above, realize immunity from the electromagnetic interference or insult. In other words, the stent has an anti-antenna geometrical shape such that the anti-antenna geometrical shape prevents the medical stent from creating an imaging artifact and/or allows the imaging of the volume within the stent.

Although the various embodiments discussed above have been described in the context of a medical stent, the various concepts and aspects of the present invention are readily applicable to other devices and uses.

For example, the pattern of electrically conductive material, according to the various concepts of the present invention, can be used in medical devices having electrically conductive structures that would, under normal circumstances, generate imaging artifacts and/or heat in response to the imaging processes, such as magnetic radiation imaging (MRI), and/or radio frequency radiation so as to make the medical devices imaging artifact immune and heat resistant. More specifically, the pattern of electrically conductive material, according to the various concepts of the present invention, could be used to create an imaging artifact immune and heat resistant mail for a doctor's glove or clothing.

While various examples and embodiments of the present invention have been shown and described, it will be appreciated by those skilled in the art that the spirit and scope of the present invention are not limited to the specific description and drawings herein, but extend to various modifications and changes.

What is claimed is:

1. A medical stent, comprising:
a pattern of electrically conductive material; and
non-conductive binding material located at areas where said electrically conductive material produces a crossover point so as to prevent a short circuit between crossing-over electrically conductive materials;
said pattern of electrically conductive material substantially preventing the medical stent from creating an imaging artifact.

2. The medical stent as claimed in claim 1, wherein said pattern is formed by multiple "figure-8" shaped electrical conductors.

3. The medical stent as claimed in claim 1, wherein said pattern is formed by multiple "figure-8" emulating electrical conductors.

4. The medical stent as claimed in claim 1, wherein said pattern is formed by multiple sine-wave-like shaped electrical conductors.

5. The medical stent as claimed in claim 1, wherein said pattern is formed by multiple zig-zag patterned electrical conductors.

6. The medical stent as claimed in claim 1, wherein said pattern is formed by multiple electrical conductors, each having sequential conductive loops.

7. The medical stent as claimed in claim 1, wherein said pattern is formed by a single conductor weaved into a loop mesh, said loop mesh being formed of two or more sequential "figure-8" shaped conductive loop pairs.

8. The medical stent as claimed in claim 7, wherein said single conductor is sine-wave-like shaped.

9. The medical stent as claimed in claim 7, wherein said single conductor is zig-zag patterned.

10. The medical stent as claimed in claim 7, wherein said single conductor is "Z"-shaped.

11. The medical stent as claimed in claim 7, wherein said single conductor is sawtooth shaped.

12. The medical stent as claimed in claim 7, wherein said single conductor is shaped to form a first-loop/direction-changing-pattern/second-loop pattern such that current induced in the first loop of said loop/direction-changing-pattern/loop pattern flows has substantially a same magnitude but opposite direction as current induced in the second loop.

13. The medical stent as claimed in claim 12, wherein said first-loop/direction-changing-pattern/second-loop pattern is a first-loop/half-hitch/second-loop pattern such that the direction changing pattern is a half hitch pattern.

14. The medical stent as claimed in claim 12, wherein said first-loop/direction-changing-pattern/second-loop pattern is repeated along a length of the medical stent.

15. The medical stent as claimed in claim 1, wherein said pattern is formed by multiple "Z"-shaped electrical conductors.

16. The medical stent as claimed in claim 1, wherein said pattern is formed by multiple sawtooth shaped electrical conductors.

17. The medical stent as claimed in claim 1, wherein said electrically conductive material is tantalum.

18. The medical stent as claimed in claim 1, wherein said electrically conductive material is nitinol.

19. The medical stent as claimed in claim 1, wherein said electrically conductive material is stainless steel.

20. The medical stent as claimed in claim 1, wherein said electrically conductive material is NbZr.

21. The medical stent as claimed in claim 1, wherein said electrically conductive material is titanium.

22. The medical stent as claimed in claim 1, wherein said non-conductive binding material providing structural support to said pattern of electrically conductive material.

23. The medical stent as claimed in claim 1, wherein said non-conductive binding material is silicon rubber.

24. The medical stent as claimed in claim 1, wherein said non-conductive binding material is a thermoplastic.

25. The medical stent as claimed in claim 1, wherein said non-conductive binding material is a thermoset polymer.

26. The medical stent as claimed in claim 1, wherein said non-conductive binding material is glass.

27. A medical stent, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially allowing imaging of a volume within the stent.

28. The medical stent as claimed in claim 27, wherein said pattern is formed by multiple "figure-8" shaped electrical conductors.

29. The medical stent as claimed in claim 27, wherein said pattern is formed by multiple "figure-8" emulating electrical conductors.

30. The medical stent as claimed in claim 27, wherein said pattern is formed by multiple sine-wave-like shaped electrical conductors.

31. The medical stent as claimed in claim 27, wherein said pattern is formed by multiple zig-zag patterned electrical conductors.

32. The medical stent as claimed in claim 27, wherein said pattern is formed by multiple electrical conductors, each having sequential conductive loops.

33. The medical stent as claimed in claim 27, wherein said pattern is formed by a single conductor weaved into a loop mesh, said loop mesh being formed of two or more sequential "figure-8" shaped conductive loop pairs.

34. The medical stent as claimed in claim 33, wherein said single conductor is sine-wave-like shaped.

35. The medical stent as claimed in claim 33, wherein said single conductor is zig-zag patterned.

36. The medical stent as claimed in claim 33, wherein said single conductor is "Z"-shaped.

37. The medical stent as claimed in claim 33, wherein said single conductor is sawtooth shaped.

38. The medical stent as claimed in claim 33, wherein said single conductor is shaped to form a first-loop/direction-changing-pattern/second-loop pattern such that current induced in the first loop of said loop/direction-changing-pattern/loop pattern flows has substantially a same magnitude but opposite direction as current induced in the second loop.

39. The medical stent as claimed in claim 38, wherein said first-loop/direction-changing-pattern/second-loop pattern is a first-loop/half-hitch/second-loop pattern such that the direction changing pattern is a half hitch pattern.

40. The medical stent as claimed in claim 38, wherein said first-loop/direction-changing-pattern/second-loop pattern is repeated along a length of the medical stent.

41. The medical stent as claimed in claim 27, wherein said pattern is formed by multiple "Z"-shaped electrical conductors.

42. The medical stent as claimed in claim 27, wherein said pattern is formed by multiple sawtooth shaped electrical conductors.

43. The medical stent as claimed in claim 27, wherein said electrically conductive material is tantalum.

44. The medical stent as claimed in claim 27, wherein said electrically conductive material is nitinol.

45. The medical stent as claimed in claim 27, wherein said electrically conductive material is stainless steel.

46. The medical stent as claimed in claim 27, wherein said electrically conductive material is NbZr.

47. The medical stent as claimed in claim 27, wherein said electrically conductive material is titanium.

48. The medical stent as claimed in claim 27, wherein said non-conductive binding material providing structural support to said pattern of electrically conductive material.

49. The medical stent as claimed in claim 27, wherein said non-conductive binding material is silicon rubber.

50. The medical stent as claimed in claim 27, wherein said non-conductive binding material is a thermoplastic.

51. The medical stent as claimed in claim 27, wherein said non-conductive binding material is a thermoset polymer.

52. The medical stent as claimed in claim 27, wherein said non-conductive binding material is glass.

53. A medical stent, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially preventing the medical stent from creating an imaging artifact and substantially allowing imaging of a volume within the stent.

54. The medical stent as claimed in claim 53, wherein said pattern is formed by multiple "figure-8" shaped electrical conductors.

55. The medical stent as claimed in claim 53, wherein said pattern is formed by multiple "figure-8" emulating electrical conductors.

56. The medical stent as claimed in claim 53, wherein said pattern is formed by multiple sine-wave-like shaped electrical conductors.

57. The medical stent as claimed in claim 53, wherein said pattern is formed by multiple zig-zag patterned electrical conductors.

58. The medical stent as claimed in claim 53, wherein said pattern is formed by multiple electrical conductors, each having sequential conductive loops.

59. The medical stent as claimed in claim 53, wherein said pattern is formed by a single conductor weaved into a loop mesh, said loop mesh being formed of two or more sequential "figure-8" shaped conductive loop pairs.

60. The medical stent as claimed in claim 59, wherein said single conductor is sine-wave-like shaped.

61. The medical stent as claimed in claim 59, wherein said single conductor is zig-zag patterned.

62. The medical stent as claimed in claim 59, wherein said single conductor is "Z"-shaped.

63. The medical stent as claimed in claim 59, wherein said single conductor is sawtooth shaped.

64. The medical stent as claimed in claim 59, wherein said single conductor is shaped to form a first-loop/direction-changing-pattern/second-loop pattern such that current induced in the first loop of said loop/direction-changing-pattern/loop pattern flows has substantially a same magnitude but opposite direction as current induced in the second loop.

65. The medical stent as claimed in claim 64, wherein said first loop/direction-changing-pattern/second-loop pattern is a first-loop/half-hitch/second-loop pattern such that the direction changing pattern is a half hitch pattern.

66. The medical stent as claimed in claim 64, wherein said first-loop/direction-changing-pattern/second-loop pattern is repeated along a length of the medical stent.

67. The medical stent as claimed in claim 53, wherein said pattern is formed by multiple "Z"-shaped electrical conductors.

68. The medical stent as claimed in claim 53, wherein said pattern is formed by multiple sawtooth shaped electrical conductors.

69. The medical stent as claimed in claim 53, wherein said electrically conductive material is tantalum.

70. The medical stent as claimed in claim 53, wherein said electrically conductive material is nitinol.

71. The medical stent as claimed in claim 53, wherein said electrically conductive material is stainless steel.

72. The medical stent as claimed in claim 53, wherein said electrically conductive material is NbZr.

73. The medical stent as claimed in claim 53, wherein said electrically conductive material is titanium.

74. The medical stent as claimed in claim 53, wherein said non-conductive binding material providing structural support to said pattern of electrically conductive material.

75. The medical stent as claimed in claim 53, wherein said non-conductive binding material is silicon rubber.

76. The medical stent as claimed in claim 53, wherein said non-conductive binding material is a thermoplastic.

77. The medical stent as claimed in claim 53, wherein said non-conductive binding material is a thermoset polymer.

78. The medical stent as claimed in claim 53, wherein said non-conductive binding material is glass.

79. An electrically conductive structure, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially prevents creation of an imaging artifact by the electrically conductive structure.

80. The electrically conductive structure as claimed in claim 79, wherein said pattern is formed by multiple "figure-8" shaped electrical conductors.

81. The electrically conductive structure as claimed in claim 79, wherein said pattern is formed by multiple sine-wave-like shaped electrical conductors.

82. The electrically conductive structure as claimed in claim 79, wherein said pattern is formed by multiple zig-zag patterned electrical conductors.

83. The electrically conductive structure as claimed in claim 79, wherein said pattern is formed by multiple electrical conductors, each having sequential conductive loops.

84. The electrically conductive structure as claimed in claim 79, wherein said pattern is formed by a single conductor weaved into a loop mesh, said loop mesh being formed of two or more sequential "figure-8" shaped conductive loop pairs.

85. The electrically conductive structure as claimed in claim 84, wherein said single conductor is sine-wave-like shaped.

86. The electrically conductive structure as claimed in claim 84, wherein said single conductor is zig-zag patterned.

87. A medical device, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially prevents creation of an imaging artifact by the medical device.

88. The medical device as claimed in claim 87, wherein said pattern is formed by multiple "figure-8" shaped electrical conductors.

89. The medical device as claimed in claim 87, wherein said pattern is formed by multiple sine-wave-like shaped electrical conductors.

90. The medical device as claimed in claim 87, wherein said pattern is formed by multiple zig-zag patterned electrical conductors.

91. The medical device as claimed in claim 87, wherein said pattern is formed by multiple electrical conductors, each having sequential conductive loops.

92. The medical device as claimed in claim 87, wherein said pattern is formed by a single conductor weaved into a loop mesh, said loop mesh being formed of two or more sequential "figure-8" shaped conductive loop pairs.

93. The medical device as claimed in claim 92, wherein said single conductor is sine-wave-like shaped.

94. The medical device as claimed in claim 92, wherein said single conductor is zig-zag patterned.

95. An electrically conductive structure, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially allows imaging of a volume within the electrically conductive structure.

96. The electrically conductive structure as claimed in claim 95, wherein said pattern is formed by multiple "figure-8" shaped electrical conductors.

97. The electrically conductive structure as claimed in claim 95, wherein said pattern is formed by multiple sine-wave-like shaped electrical conductors.

98. The electrically conductive structure as claimed in claim 95, wherein said pattern is formed by multiple zig-zag patterned electrical conductors.

99. The electrically conductive structure as claimed in claim 95, wherein said pattern is formed by multiple electrical conductors, each having sequential conductive loops.

100. The electrically conductive structure as claimed in claim 95, wherein said pattern is formed by a single conductor weaved into a loop mesh, said loop mesh being formed of two or more sequential "figure-8" shaped conductive loop pairs.

101. The electrically conductive structure as claimed in claim 100, wherein said single conductor is sine-wave-like shaped.

102. The electrically conductive structure as claimed in claim 100, wherein said single conductor is zig-zag patterned.

103. An electrically conductive structure, comprising:
a pattern of electrically conductive material; and
non-conductive binding material located at areas where said electrically conductive material produces a cross-over point so as to prevent a short circuit between crossing-over electrically conductive materials;
said pattern of electrically conductive material substantially prevents creation of an imaging artifact by the medical device and substantially allows imaging of a volume within the electrically conductive structure.

104. The electrically conductive structure as claimed in claim 103, wherein said pattern is formed by multiple "figure-8" shaped electrical conductors.

105. The electrically conductive structure as claimed in claim 103, wherein said pattern is formed by multiple sine-wave-like shaped electrical conductors.

106. The electrically conductive structure as claimed in claim 103, wherein said pattern is formed by multiple zig-zag patterned electrical conductors.

107. The electrically conductive structure as claimed in claim 103, wherein said pattern is formed by multiple electrical conductors, each having sequential conductive loops.

108. The electrically conductive structure as claimed in claim 103, wherein said pattern is formed by a single conductor weaved into a loop mesh, said loop mesh being formed of two or more sequential "figure-8" shaped conductive loop pairs.

109. The electrically conductive structure as claimed in claim 108, wherein said single conductor is sine-wave-like shaped.

110. The electrically conductive structure as claimed in claim 108, wherein said single conductor is zig-zag patterned.

111. A medical device, comprising:
a pattern of electrically conductive material; and
non-conductive binding material located at areas where said electrically conductive material produces a crossover point so as to prevent a short circuit between crossing-over electrically conductive materials;
said pattern of electrically conductive material substantially allows imaging of a volume within the medical device.

112. The medical device as claimed in claim 111, wherein said pattern is formed by multiple "figure-8" shaped electrical conductors.

113. The medical device as claimed in claim 111, wherein said pattern is formed by multiple sine-wave-like shaped electrical conductors.

114. The medical device as claimed in claim 111, wherein said pattern is formed by multiple zig-zag patterned electrical conductors.

115. The medical device as claimed in claim 111, wherein said pattern is formed by multiple electrical conductors, each having sequential conductive loops.

116. The medical device as claimed in claim 111, wherein said pattern is formed by a single conductor weaved into a loop mesh, said loop mesh being formed of two or more sequential "figure-8" shaped conductive loop pairs.

117. The medical device as claimed in claim 116, wherein said single conductor is sine-wave-like shaped.

118. The medical device as claimed in claim 116, wherein said single conductor is zig-zag patterned.

119. A medical device, comprising:
a pattern of electrically conductive material; and
non-conductive binding material located at areas where said electrically conductive material produces a crossover point so as to prevent a short circuit between crossing-over electrically conductive materials;
said pattern of electrically conductive material having an anti-antenna geometrical shape such that said anti-antenna geometrical shape substantially prevents creation of an imaging artifact by the medical device and substantially allows imaging of a volume within the medical device.

120. The medical device as claimed in claim 119, wherein said pattern is formed by multiple "figure-8" shaped electrical conductors.

121. The medical device as claimed in claim 119, wherein said pattern is formed by multiple sine-wave-like shaped electrical conductors.

122. The medical device as claimed in claim 119, wherein said pattern is formed by multiple zig-zag patterned electrical conductors.

123. The medical device as claimed in claim 119, wherein said pattern is formed by multiple electrical conductors, each having sequential conductive loops.

124. The medical device as claimed in claim 119, wherein said pattern is formed by a single conductor weaved into a loop mesh, said loop mesh being formed of two or more sequential "figure-8" shaped conductive loop pairs.

125. The medical device as claimed in claim 124, wherein said single conductor is sine-wave-like shaped.

126. The medical device as claimed in claim 124, wherein said single conductor is zig-zag patterned.

* * * * *